(12) United States Patent
Pérez et al.

(10) Patent No.: US 8,076,297 B2
(45) Date of Patent: Dec. 13, 2011

(54) PHARMACEUTICAL COMPOSITION CONTAINING POLYPEPTIDE FRAGMENTS OF SERRALYSINS

(75) Inventors: Maria del Carmen Abrahantes Pérez, Ciudad de la Habana (CU); Jesús Reyes González, Ciudad de la Habana (CU); Gloria Véliz Rios, Cuidad de la Habana (CU); Eduardo Martinez Diaz, Ciudad de la Habana (CU); Caridad Anais Gasmuri González, Ciudad de la Habana (CU); José Garcia Suárez, Ciudad de la Habana (CU); Mónica Bequet Romero, Ciudad de la Habana (CU); Luis Javier González López, Ciudad de la Habana (CU); Lila Rosa Castellanos Serra, Ciudad de la Habana (CU); Manuel Selman-Housein Sosa, Ciudad de la Habana (CU); Raúl Gómez Riera, Ciudad de la Habana (CU); Jorge Victor Gavilondo Cowley, Ciudad de la Habana (CU)

(73) Assignee: Centro De Ingenieria Genetica Y Biotecnologia, Cuidad de La Habana (CU)

( * ) Notice: Subject to any disclaimer, the term of this patent is extended or adjusted under 35 U.S.C. 154(b) by 1033 days.

(21) Appl. No.: 11/631,880

(22) PCT Filed: Jul. 5, 2005
(Under 37 CFR 1.47)

(86) PCT No.: PCT/CU2005/000003
§ 371 (c)(1),
(2), (4) Date: Dec. 13, 2007

(87) PCT Pub. No.: WO2006/005268
PCT Pub. Date: Jan. 19, 2006

(65) Prior Publication Data
US 2011/0218138 A1    Sep. 8, 2011

(30) Foreign Application Priority Data
Jul. 8, 2004    (CU) .................................. 2004-0147

(51) Int. Cl.
*A61K 38/43*    (2006.01)
*C12N 9/52*    (2006.01)

(52) U.S. Cl. .................. 514/19.3; 514/21.2; 435/220

(58) Field of Classification Search .................. None
See application file for complete search history.

(56) References Cited

U.S. PATENT DOCUMENTS
2004/0185566 A1    9/2004    Salamone

FOREIGN PATENT DOCUMENTS
EP          0226800 A      7/1987
FR          2519021 A      7/1983
WO          WO 99/15690 A  4/1999

*Primary Examiner* — Christina Bradley
(74) *Attorney, Agent, or Firm* — Hoffman & Baron, LLP

(57) ABSTRACT

The present invention is related to a composition capable of inhibiting the growth of tumoral cells of different histological origins and of activated endothelial cells. The components of said compositions are polypeptide fragments of the serralisins, corresponding to the C-terminal fragment, from the internal metionine trough the end of the molecule, which could be combined among them and optionally with the prodigiosins that potentiate the antitumoral effect of the composition. The prodigiosins in the composition could be at a concentration of 0.1-100 nM. The anti-proliferative action of this composition is mediated by apoptotic mechanism. It's "in vivo" administration has antitumoral, antiangiogenic and protective effect against malignant tumors.

6 Claims, 16 Drawing Sheets

A

B

A

B

A

B

SEQUENCE LISTING

<160> NUMBER OF SEQ ID NOS: 16

<210> SEQ ID NO 1
<211> LENGTH: 258

```
<212> TYPE: PRT
<213> ORGANISM: Serratia marcescens
<220> FEATURE:
<221> NAME/KEY: PEPTIDE
<222> LOCATION: (1)..(258)
<223> OTHER INFORMATION: Sequence of the C-terminal of the SERMA
      Serralysin

<400> SEQUENCE: 1

Met Ser Tyr Trp Ser Glu Thr Asn Thr Gly Gly Asp Asn Gly Gly His
1               5                   10                  15

Tyr Ala Ala Ala Pro Leu Leu Asp Asp Ile Ala Ala Ile Gln His Leu
            20                  25                  30

Tyr Gly Ala Asn Pro Ser Thr Arg Thr Gly Asp Thr Val Tyr Gly Phe
        35                  40                  45

Asn Ser Asn Thr Gly Arg Asp Phe Leu Ser Thr Ser Asn Ser Gln
    50                  55                  60

Lys Val Ile Phe Ala Ala Trp Asp Ala Gly Asn Asp Thr Phe Asp
65                  70                  75                  80

Phe Ser Gly Tyr Thr Ala Asn Gln Arg Ile Asn Leu Asn Glu Lys Ser
                85                  90                  95

Phe Ser Asp Val Gly Gly Leu Lys Gly Asn Val Ser Ile Ala Ala Gly
            100                 105                 110

Val Thr Ile Glu Asn Ala Ile Gly Gly Ser Gly Asn Asp Val Ile Val
        115                 120                 125

Gly Asn Ala Ala Asn Asn Val Leu Lys Gly Gly Ala Gly Asn Asp Val
    130                 135                 140

Leu Phe Gly Gly Gly Gly Ala Asp Glu Leu Trp Gly Gly Ala Gly Lys
145                 150                 155                 160

Asp Ile Phe Val Phe Ser Ala Ala Ser Asp Ser Ala Pro Gly Ala Ser
                165                 170                 175

Asp Trp Ile Arg Asp Phe Gln Lys Gly Ile Asp Lys Ile Asp Leu Ser
            180                 185                 190

Phe Phe Asn Lys Glu Ala Asn Ser Ser Asp Phe Ile His Phe Val Asp
        195                 200                 205

His Phe Ser Gly Thr Ala Gly Glu Ala Leu Leu Ser Tyr Asn Ala Ser
    210                 215                 220

Ser Asn Val Thr Asp Leu Ser Val Asn Ile Gly Gly His Gln Ala Pro
225                 230                 235                 240

Asp Phe Leu Val Lys Ile Val Gly Gln Val Asp Val Ala Thr Asp Phe
                245                 250                 255

Ile Val

<210> SEQ ID NO 2
<211> LENGTH: 257
<212> TYPE: PRT
<213> ORGANISM: Serratia marcescens
<220> FEATURE:
<221> NAME/KEY: PEPTIDE
<222> LOCATION: (1)..(257)
<223> OTHER INFORMATION: C-terminal Sequence of the SERSP Serralysin

<400> SEQUENCE: 2

Met Ser Tyr Trp Ser Glu Thr Asn Thr Gly Gly Asp Asn Gly Gly His
1               5                   10                  15

Tyr Ala Ala Ala Pro Leu Leu Asp Asp Ile Ala Ala Ile Gln His Leu
            20                  25                  30

Tyr Gly Ala Asn Leu Ser Thr Arg Thr Gly Asp Thr Val Tyr Gly Phe
        35                  40                  45
```

```
Asn Ser Asn Thr Gly Arg Asp Phe Leu Ser Thr Thr Ser Asn Ser Gln
     50                  55                  60

Lys Val Ile Phe Ala Ala Trp Asp Ala Gly Gly Asn Asp Thr Phe Asp
 65                  70                  75                  80

Phe Ser Gly Tyr Thr Ala Asn Gln Arg Ile Asn Leu Asn Glu Lys Ser
                 85                  90                  95

Phe Ser Asp Val Gly Gly Leu Lys Gly Asn Val Ser Ile Ala Ala Gly
            100                 105                 110

Val Thr Ile Glu Asn Ala Ile Gly Phe Arg Gln Arg Leu Ile Val Gly
        115                 120                 125

Asn Ala Ala Asn Asn Val Leu Lys Gly Gly Ala Gly Asn Asp Val Leu
    130                 135                 140

Phe Gly Gly Gly Gly Ala Asp Glu Leu Trp Gly Gly Ala Gly Lys Asp
145                 150                 155                 160

Ile Phe Val Phe Ser Ala Ala Ser Asp Ser Ala Pro Gly Ala Ser Asp
                165                 170                 175

Trp Ile Arg Asp Phe Gln Lys Gly Ile Asp Lys Ile Asp Leu Ser Phe
            180                 185                 190

Phe Asn Lys Glu Ala Gln Ser Ser Asp Phe Ile His Phe Val Asp His
        195                 200                 205

Phe Ser Gly Ala Ala Gly Glu Ala Leu Leu Ser Tyr Asn Ala Ser Asn
    210                 215                 220

Asn Val Thr Asp Leu Ser Val Asn Ile Gly Gly His Gln Ala Pro Asp
225                 230                 235                 240

Phe Leu Val Lys Ile Val Gly Gln Val Asp Val Ala Thr Asp Phe Ile
                245                 250                 255

Val

<210> SEQ ID NO 3
<211> LENGTH: 219
<212> TYPE: PRT
<213> ORGANISM: Serratia marcescens
<220> FEATURE:
<221> NAME/KEY: PEPTIDE
<222> LOCATION: (1)..(219)
<223> OTHER INFORMATION: C-terminal Sequence of the SERSP Serralysin

<400> SEQUENCE: 3

Thr Arg Thr Gly Asp Thr Val Tyr Gly Phe Asn Ser Asn Thr Gly Arg
 1               5                  10                  15

Asp Phe Leu Ser Thr Thr Ser Asn Ser Gln Lys Val Ile Phe Ala Ala
            20                  25                  30

Trp Asp Ala Gly Gly Asn Asp Thr Phe Asp Phe Ser Gly Tyr Thr Ala
        35                  40                  45

Asn Gln Arg Ile Asn Leu Asn Glu Lys Ser Phe Ser Asp Val Gly Gly
    50                  55                  60

Leu Lys Gly Asn Val Ser Ile Ala Ala Gly Val Thr Ile Glu Asn Ala
 65                  70                  75                  80

Ile Gly Phe Arg Gln Arg Leu Ile Val Gly Asn Ala Ala Asn Asn Val
                 85                  90                  95

Leu Lys Gly Gly Ala Gly Asn Asp Val Leu Phe Gly Gly Gly Gly Ala
            100                 105                 110

Asp Glu Leu Trp Gly Gly Ala Gly Lys Asp Ile Phe Val Phe Ser Ala
        115                 120                 125

Ala Ser Asp Ser Ala Pro Gly Ala Ser Asp Trp Ile Arg Asp Phe Gln
    130                 135                 140
```

```
Lys Gly Ile Asp Lys Ile Asp Leu Ser Phe Phe Asn Lys Glu Ala Gln
145                 150                 155                 160

Ser Ser Asp Phe Ile His Phe Val Asp His Phe Ser Gly Ala Ala Gly
                165                 170                 175

Glu Ala Leu Leu Ser Tyr Asn Ala Ser Asn Asn Val Thr Asp Leu Ser
                180                 185                 190

Val Asn Ile Gly Gly His Gln Ala Pro Asp Phe Leu Val Lys Ile Val
            195                 200                 205

Gly Gln Val Asp Val Ala Thr Asp Phe Ile Val
        210                 215

<210> SEQ ID NO 4
<211> LENGTH: 220
<212> TYPE: PRT
<213> ORGANISM: Serratia marcescens
<220> FEATURE:
<221> NAME/KEY: PEPTIDE
<222> LOCATION: (1)..(220)
<223> OTHER INFORMATION: C-terminal Sequence of the SERMA Serralysin

<400> SEQUENCE: 4

Thr Arg Thr Gly Asp Thr Val Tyr Gly Phe Asn Ser Asn Thr Gly Arg
1               5                   10                  15

Asp Phe Leu Ser Thr Thr Ser Asn Ser Gln Lys Val Ile Phe Ala Ala
            20                  25                  30

Trp Asp Ala Gly Gly Asn Asp Thr Phe Asp Phe Ser Gly Tyr Thr Ala
        35                  40                  45

Asn Gln Arg Ile Asn Leu Asn Glu Lys Ser Phe Ser Asp Val Gly Gly
    50                  55                  60

Leu Lys Gly Asn Val Ser Ile Ala Ala Gly Val Thr Ile Glu Asn Ala
65                  70                  75                  80

Ile Gly Gly Ser Gly Asn Asp Val Ile Val Gly Asn Ala Ala Asn Asn
                85                  90                  95

Val Leu Lys Gly Gly Ala Gly Asn Asp Val Leu Phe Gly Gly Gly Gly
            100                 105                 110

Ala Asp Glu Leu Trp Gly Gly Ala Gly Lys Asp Ile Phe Val Phe Ser
        115                 120                 125

Ala Ala Ser Asp Ser Ala Pro Gly Ala Ser Asp Trp Ile Arg Asp Phe
    130                 135                 140

Gln Lys Gly Ile Asp Lys Ile Asp Leu Ser Phe Phe Asn Lys Glu Ala
145                 150                 155                 160

Asn Ser Ser Asp Phe Ile His Phe Val Asp His Phe Ser Gly Thr Ala
                165                 170                 175

Gly Glu Ala Leu Leu Ser Tyr Asn Ala Ser Ser Asn Val Thr Asp Leu
            180                 185                 190

Ser Val Asn Ile Gly Gly His Gln Ala Pro Asp Phe Leu Val Lys Ile
        195                 200                 205

Val Gly Gln Val Asp Val Ala Thr Asp Phe Ile Val
    210                 215                 220

<210> SEQ ID NO 5
<211> LENGTH: 5
<212> TYPE: PRT
<213> ORGANISM: Serratia marcescens
<220> FEATURE:
<221> NAME/KEY: PEPTIDE
<222> LOCATION: (1)..(5)
<223> OTHER INFORMATION: Serralysin Sequence
```

```
<400> SEQUENCE: 5

Ala Gln Glu Asn Ser
1               5

<210> SEQ ID NO 6
<211> LENGTH: 4
<212> TYPE: PRT
<213> ORGANISM: Serratia marcescens
<220> FEATURE:
<221> NAME/KEY: PEPTIDE
<222> LOCATION: (1)..(4)
<223> OTHER INFORMATION: Serralysin Sequence

<400> SEQUENCE: 6

Thr Phe Ser Phe
1

<210> SEQ ID NO 7
<211> LENGTH: 4
<212> TYPE: PRT
<213> ORGANISM: Serratia marcescens
<220> FEATURE:
<221> NAME/KEY: PEPTIDE
<222> LOCATION: (1)..(4)
<223> OTHER INFORMATION: Xaa can be any amino acid

<400> SEQUENCE: 7

Gly Gly Phe Xaa
1

<210> SEQ ID NO 8
<211> LENGTH: 11
<212> TYPE: PRT
<213> ORGANISM: Serratia marcescens
<220> FEATURE:
<221> NAME/KEY: PEPTIDE
<222> LOCATION: (1)..(11)
<223> OTHER INFORMATION: Serralysin Sequence

<400> SEQUENCE: 8

Asp Phe Leu Ser Thr Thr Ser Asn Ser Gln Lys
1               5                   10

<210> SEQ ID NO 9
<211> LENGTH: 15
<212> TYPE: PRT
<213> ORGANISM: Serratia marcescens
<220> FEATURE:
<221> NAME/KEY: PEPTIDE
<222> LOCATION: (1)..(15)
<223> OTHER INFORMATION: Serralysin Sequence

<400> SEQUENCE: 9

Ser Ala Ala Ser Asp Ser Ala Pro Gly Ala Ser Asp Trp Ile Arg
1               5                   10                  15

<210> SEQ ID NO 10
<211> LENGTH: 23
<212> TYPE: PRT
<213> ORGANISM: Serratia marcescens
<220> FEATURE:
<221> NAME/KEY: PEPTIDE
<222> LOCATION: (1)..(23)
<223> OTHER INFORMATION: Serralysin Sequence

<400> SEQUENCE: 10

Gly Gly Ala Gly Asn Asp Val Leu Phe Gly Gly Gly Ala Asp Glu
1               5                   10                  15
```

```
Leu Trp Gly Gly Ala Gly Lys
            20

<210> SEQ ID NO 11
<211> LENGTH: 14
<212> TYPE: PRT
<213> ORGANISM: Serratia marcescens
<220> FEATURE:
<221> NAME/KEY: PEPTIDE
<222> LOCATION: (1)..(14)
<223> OTHER INFORMATION: Serralysin Sequence

<400> SEQUENCE: 11

Thr Gly Asp Thr Val Tyr Gly Phe Asn Ser Asn Thr Gly Arg
1               5                   10

<210> SEQ ID NO 12
<211> LENGTH: 9
<212> TYPE: PRT
<213> ORGANISM: Serratia marcescens
<220> FEATURE:
<221> NAME/KEY: PEPTIDE
<222> LOCATION: (1)..(9)
<223> OTHER INFORMATION: Serralysin Sequence

<400> SEQUENCE: 12

Ser Phe Ser Asp Val Gly Gly Leu Lys
1               5

<210> SEQ ID NO 13
<211> LENGTH: 8
<212> TYPE: PRT
<213> ORGANISM: Serratia marcescens
<220> FEATURE:
<221> NAME/KEY: PEPTIDE
<222> LOCATION: (1)..(8)
<223> OTHER INFORMATION: Serralysin Sequence

<400> SEQUENCE: 13

Ile Asp Leu Ser Phe Phe Asn Lys
1               5

<210> SEQ ID NO 14
<211> LENGTH: 13
<212> TYPE: PRT
<213> ORGANISM: Serratia marcescens
<220> FEATURE:
<221> NAME/KEY: PEPTIDE
<222> LOCATION: (1)..(13)
<223> OTHER INFORMATION: Serralysin Sequence

<400> SEQUENCE: 14

Ile Val Gly Gln Val Asp Val Ala Thr Asp Phe Ile Val
1               5                   10

<210> SEQ ID NO 15
<211> LENGTH: 487
<212> TYPE: PRT
<213> ORGANISM: Serratia marcescens
<220> FEATURE:
<221> NAME/KEY: PEPTIDE
<222> LOCATION: (1)..(487)
<223> OTHER INFORMATION: SERMA Serralysin sequence

<400> SEQUENCE: 15

Met Gln Ser Thr Lys Lys Ala Ile Glu Ile Thr Glu Ser Ser Leu Ala
1               5                   10                  15

Ala Ala Thr Thr Gly Tyr Asp Ala Val Asp Asp Leu Leu His Tyr His
            20                  25                  30
```

-continued

```
Glu Arg Gly Asn Gly Ile Gln Ile Asn Gly Lys Asp Ser Phe Ser Asn
             35                  40                  45

Glu Gln Ala Gly Leu Phe Ile Thr Arg Glu Asn Gln Thr Trp Asn Gly
 50                  55                  60

Tyr Lys Val Phe Gly Gln Pro Val Lys Leu Thr Phe Ser Phe Pro Asp
 65                  70                  75                  80

Tyr Lys Phe Ser Ser Thr Asn Val Ala Gly Asp Thr Gly Leu Ser Lys
                 85                  90                  95

Phe Ser Ala Glu Gln Gln Gln Ala Lys Leu Ser Leu Gln Ser Trp
            100                 105                 110

Ala Asp Val Ala Asn Ile Thr Phe Thr Glu Val Ala Ala Gly Gln Lys
            115                 120                 125

Ala Asn Ile Thr Phe Gly Asn Tyr Ser Gln Asp Arg Pro Gly His Tyr
            130                 135                 140

Asp Tyr Gly Thr Gln Ala Tyr Ala Phe Leu Pro Asn Thr Ile Trp Gln
145                 150                 155                 160

Gly Gln Asp Leu Gly Gly Gln Thr Trp Tyr Asn Val Asn Gln Ser Asn
                165                 170                 175

Val Lys His Pro Ala Thr Glu Asp Tyr Gly Arg Gln Thr Phe Thr His
            180                 185                 190

Glu Ile Gly His Ala Leu Gly Leu Ser His Pro Gly Asp Tyr Asn Ala
            195                 200                 205

Gly Glu Gly Asn Pro Thr Tyr Asn Asp Val Thr Tyr Ala Glu Asp Thr
            210                 215                 220

Arg Gln Phe Ser Leu Met Ser Tyr Trp Ser Glu Thr Asn Thr Gly Gly
225                 230                 235                 240

Asp Asn Gly Gly His Tyr Ala Ala Ala Pro Leu Leu Asp Asp Ile Ala
                245                 250                 255

Ala Ile Gln His Leu Tyr Gly Ala Asn Pro Ser Thr Arg Thr Gly Asp
            260                 265                 270

Thr Val Tyr Gly Phe Asn Ser Asn Thr Gly Arg Asp Phe Leu Ser Thr
            275                 280                 285

Thr Ser Asn Ser Gln Lys Val Ile Phe Ala Ala Trp Asp Ala Gly Gly
            290                 295                 300

Asn Asp Thr Phe Asp Phe Ser Gly Tyr Thr Ala Asn Gln Arg Ile Asn
305                 310                 315                 320

Leu Asn Glu Lys Ser Phe Ser Asp Val Gly Gly Leu Lys Gly Asn Val
                325                 330                 335

Ser Ile Ala Ala Gly Val Thr Ile Glu Asn Ala Ile Gly Gly Ser Gly
            340                 345                 350

Asn Asp Val Ile Val Gly Asn Ala Ala Asn Asn Val Leu Lys Gly Gly
            355                 360                 365

Ala Gly Asn Asp Val Leu Phe Gly Gly Gly Ala Asp Glu Leu Trp
            370                 375                 380

Gly Gly Ala Gly Lys Asp Ile Phe Val Phe Ser Ala Ala Ser Asp Ser
385                 390                 395                 400

Ala Pro Gly Ala Ser Asp Trp Ile Arg Asp Phe Gln Lys Gly Ile Asp
                405                 410                 415

Lys Ile Asp Leu Ser Phe Phe Asn Lys Glu Ala Asn Ser Ser Asp Phe
            420                 425                 430

Ile His Phe Val Asp His Phe Ser Gly Thr Ala Gly Glu Ala Leu Leu
            435                 440                 445

Ser Tyr Asn Ala Ser Ser Asn Val Thr Asp Leu Ser Val Asn Ile Gly
```

```
              450                 455                 460
Gly His Gln Ala Pro Asp Phe Leu Val Lys Ile Val Gly Gln Val Asp
465                 470                 475                 480

Val Ala Thr Asp Phe Ile Val
                485

<210> SEQ ID NO 16
<211> LENGTH: 486
<212> TYPE: PRT
<213> ORGANISM: Serratia marcescens
<220> FEATURE:
<221> NAME/KEY: PEPTIDE
<222> LOCATION: (1)..(486)
<223> OTHER INFORMATION: SERSP Serralysin sequence

<400> SEQUENCE: 16

Met Gln Ser Thr Lys Lys Ala Ile Glu Ile Thr Glu Ser Asn Phe Ala
1               5                   10                  15

Ala Ala Thr Thr Gly Tyr Asp Ala Val Asp Asp Leu Leu His Tyr His
                20                  25                  30

Glu Arg Gly Asn Gly Ile Gln Ile Asn Gly Lys Asp Ser Phe Ser Asn
            35                  40                  45

Glu Gln Ala Gly Leu Phe Ile Thr Arg Glu Asn Gln Thr Trp Asn Gly
        50                  55                  60

Tyr Lys Val Phe Gly Gln Pro Val Lys Leu Thr Phe Ser Phe Pro Asp
65                  70                  75                  80

Tyr Lys Phe Ser Ser Thr Asn Val Ala Gly Asp Thr Gly Leu Ser Lys
                85                  90                  95

Phe Ser Ala Glu Gln Gln Gln Gln Ala Lys Leu Ser Leu Gln Ser Trp
            100                 105                 110

Ala Asp Val Ala Asn Ile Thr Phe Thr Glu Val Ala Ala Gly Gln Lys
        115                 120                 125

Ala Asn Ile Thr Phe Gly Asn Tyr Ser Gln Asp Arg Pro Gly His Tyr
    130                 135                 140

Asp Tyr Gly Thr Gln Ala Tyr Ala Phe Leu Pro Asn Thr Ile Trp Gln
145                 150                 155                 160

Gly Gln Asp Leu Gly Gly Gln Thr Trp Tyr Asn Val Asn Gln Ser Asn
                165                 170                 175

Val Lys His Pro Ala Thr Glu Asp Tyr Gly Arg Gln Thr Phe Thr His
            180                 185                 190

Glu Ile Gly His Ala Leu Gly Leu Ser His Pro Gly Asp Tyr Asn Ala
        195                 200                 205

Gly Glu Gly Asn Pro Thr Tyr Arg Asp Val Thr Tyr Ala Glu Asp Thr
    210                 215                 220

Arg Gln Phe Ser Leu Met Ser Tyr Trp Ser Glu Thr Asn Thr Gly Gly
225                 230                 235                 240

Asp Asn Gly Gly His Tyr Ala Ala Ala Pro Leu Leu Asp Asp Ile Ala
                245                 250                 255

Ala Ile Gln His Leu Tyr Gly Ala Asn Leu Ser Thr Arg Thr Gly Asp
            260                 265                 270

Thr Val Tyr Gly Phe Asn Ser Asn Thr Gly Arg Asp Phe Leu Ser Thr
        275                 280                 285

Thr Ser Asn Ser Gln Lys Val Ile Phe Ala Ala Trp Asp Ala Gly Gly
    290                 295                 300

Asn Asp Thr Phe Asp Phe Ser Gly Tyr Thr Ala Asn Gln Arg Ile Asn
305                 310                 315                 320
```

-continued

```
Leu Asn Glu Lys Ser Phe Ser Asp Val Gly Gly Leu Lys Gly Asn Val
            325                 330                 335

Ser Ile Ala Ala Gly Val Thr Ile Glu Asn Ala Ile Gly Phe Arg Gln
            340                 345                 350

Arg Leu Ile Val Gly Asn Ala Ala Asn Asn Val Leu Lys Gly Gly Ala
            355                 360                 365

Gly Asn Asp Val Leu Phe Gly Gly Gly Ala Asp Glu Leu Trp Gly
        370                 375                 380

Gly Ala Gly Lys Asp Ile Phe Val Phe Ser Ala Ala Ser Asp Ser Ala
385                 390                 395                 400

Pro Gly Ala Ser Asp Trp Ile Arg Asp Phe Gln Lys Gly Ile Asp Lys
                405                 410                 415

Ile Asp Leu Ser Phe Phe Asn Lys Glu Ala Gln Ser Ser Asp Phe Ile
            420                 425                 430

His Phe Val Asp His Phe Ser Gly Ala Ala Gly Glu Ala Leu Leu Ser
            435                 440                 445

Tyr Asn Ala Ser Asn Asn Val Thr Asp Leu Ser Val Asn Ile Gly Gly
        450                 455                 460

His Gln Ala Pro Asp Phe Leu Val Lys Ile Val Gly Gln Val Asp Val
465                 470                 475                 480

Ala Thr Asp Phe Ile Val
                485
```

PHARMACEUTICAL COMPOSITION CONTAINING POLYPEPTIDE FRAGMENTS OF SERRALYSINS

Figure 1:
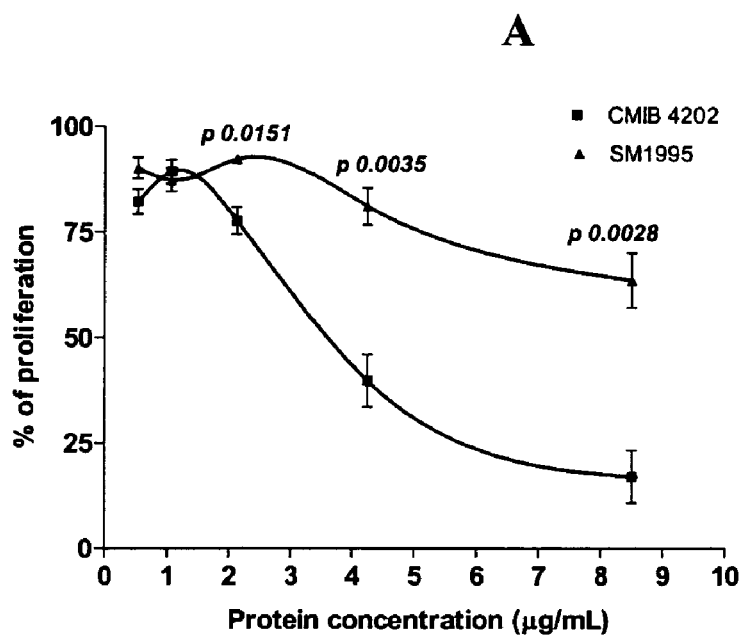
Figure 1:
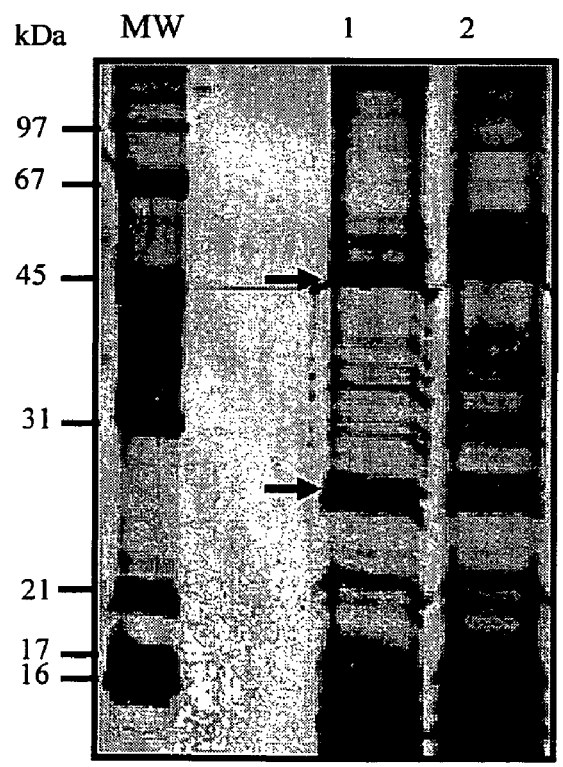

This application is the U.S. National Phase of, and Applicants claim priority from, International Application Number PCT/CU2005/000003 filed 5 Jul. 2005 and Cuban Patent Application bearing Serial No. CU 2004-0147 filed 8 Jul. 2004, which are incorporated herein by reference.

FIELD OF THE INVENTION

The present invention is related to the field of biotechnology, the pharmaceutical industry and in particular with the production of a composition capable of inhibit the growth of tumoral cells. This composition contains polypeptides fragments from Serralisins, obtained from the degradation of the intact protein, which have a higher antiproliferative activity that the whole serralisin molecules. Said fragments belong to the C-terminal of the serralisins, from the internal metionine of the sequence to the end of the molecule, and the combination of the same with prodigiosins enhance the anti-tumoral effect of this composition.

PRIOR ART

Cancer chemotherapy has been traditionally directed to the inhibition of cancer cells proliferation. Nevertheless, in the last years the interest in antitumoral products that induce apoptosis, has increase because cancer has been establish as a pathology related to a relative deficiency in apoptosis, instead of an excess of proliferation.

Bacteria or their extracts have been used for cancer treatment for almost 100 years. The must quoted report is from the physician and surgeon William B. Coley from the Memorial Hospital in New Cork city call Sloan-Kettering Memorial Hospital. He observed that many of his patient with several types of cancer experience tumor regression after been infected by pathogenic bacteria. (Coley, W. B. 1991—reprinted from 1893—. Clin. Orthop. 262:3).

Resistance to tumors on patients or animals infected was attributed to the concomitant cell mediated antitumoral immunity (Paglia, P. and Guzmán, C. A. 1998. Cancer immunol. Immunother. 46:88). The idea that a pathogenic bacterial or protozoan infection could activate cancer regression through the activation of the innate or adaptative immunity has been recently questioned by Hunter et al. (Hunter, C. A., Yu, D., Gee, M., Ngo, C. V., Sevignani, C., Goldschmidt, M., Golovkina, T. V., Evans, S., Lee, W. F. and Thomas-Tekhonenko, A. 2001. J. Immunol. 166:5878). They demonstrated that the tissues infected by *T. Gondii* produce some soluble antiangiogenic factors that avoid the formation of blood vessels in the tumors, which could be of potential therapeutic interest. This process of formation of new capillaries known as angiogenesis, has became an important focus of attention for the implementation of new therapies for cancer and their metastases. The search for antiangiogenic factors is the foundation of new anticancer therapeutic strategies (Folkman, J. 2003. Seminars in Cancer Biology. 13:159). Recently the use of anaerobic bacteria as chemotherapeutic and selective antivascular agents has resulted in a significative regression of subcutaneous (sc) tumors in mice. This treatment is named combined bacteriolytic therapy (CO-BALTO) (Dang, L. H., Bettegowda, C., Huso, D. L., Klnzler, K. W. and Vogelstein, B. 2001. Proc Natl Arad Sci USA. 98: 15155). Nevertheless, live bacteria produce important toxicity and collateral reactions that limit their use against human cancer.

In the last years, some reports has appear that indicate that anaerobic bacterias release redox proteins that induce tumor cells apoptosis (Yamada, T., Goto, M., Punj, V., Zaborina, O. and Chen, M. L. 2002. Proc. Natl. Acad. Sci. USA. 99: 14088; Goto, M., Yamada, T., Kimbara, K., Horner, J., Newcomb, M., Gupta, T. K. and Chakrabarty, A. M. 2003. Mol Microbiol. 47:549). It has been postulated that redox proteins could be included in a group of soluble proteins that were secreted by prokaryotic cells ancestors, and their functions could have been the elimination of ancestral eukaryotic cells (Punj, V. and Chakrabarty, A. M. 2003. Cellular Microbiology. 5:225). In general little is known about the production of soluble secreted factors by these prokaryotic organisms that could act in an specific manner on cancer cells, causing their death and concomitantly, the tumor regression.

*Serratia marcescens* is a facultative anaerobic bacteria. From some of its strains some preparations have been obtained with antitumoral properties, the most studied are: [a] ImuVert® (Budagov, R. S. and Ulianova, L. P. 2001. Radiats Biol Radioecol Russian. 41:38), a preparation of ribosomal membranes that activate the patient's immune system; [b] the Serratial protease Mr 56,000 (Wu, J., Akaike, T., Hayashida, K., Okamoto, T., Okuyama, A. and Maeda, H. 2001. Jpn. J. Cancer Res. 92:439), which induce the cells death by necrosis depending on the expression of α-2 macroglobuline; and [c] the prodigiosins, a family of pigments that act as immunesupressors and anticancerigens through the induction of apoptosis (Montaner, B and Pérez Tomas, R. 2003. Curr Cancer Drug Targets. 3:57; Pérez Tomas, R. y Montaner, B. 2003. Histol Histopathol. 18:379).

We have obtained non-proteolytic fragments of serralisins with higher cytotoxic activity than the entire molecules. This allows to combine these fragments with low doses of prodigiosine, lowering the toxicity reported for the pigment and increasing the antiproliferative effect on tumoral cells.

DETAIL DESCRIPTION OF THE INVENTION

The compositions of this invention are able to inhibit the growth of tumoral cells and are formed by polypeptyde fragments of serralisins, with higher antiproliferative effect than the entire serralisins molecules, which can be combined with prodigiosines that enhance their antitumoral effect.

In this invention is described the obtention of the MG2327 preparation, were coexist both polypeptides and prodigiosins, that have a wide spectrum of cytotoxic activity on malignant cell lines, with selective effect on transformed tumoral cells and specifically on cells activated for their growth. The sensibility study on different cell lines, tumoral or not, demonstrate that normal cell lines are only slightly sensitive to the MG2327 preparation, while cells derived from melanoma, laringela carcinoma, fibrosarcomes, hepatocarcinomes and cervico-uterine carcinoma (positive or not for human papilloma virus) are very sensitives. The carcinomas of haematopoyetical origin are less sensitive. HUVEC cells activated for their growth are more sensitive to MG2327 that those no activated. MG2327 preparation is able to act specifically on factor expressed or over expressed during the process of cell division. These factors constitute therapeutical targets against cancer or other diseases of proliferative origins. Furthermore, these factors also constitute targets for the early diagnosis of diseases originated by an excess of proliferation, or by the not controlled proliferation of differentiated or non-differentiated cells. Controlled release formulations containing these molecules could be directed to these proliferating targets acting in a specific manner upon them; because normal cells are more resistant to its action.

Figure 8:
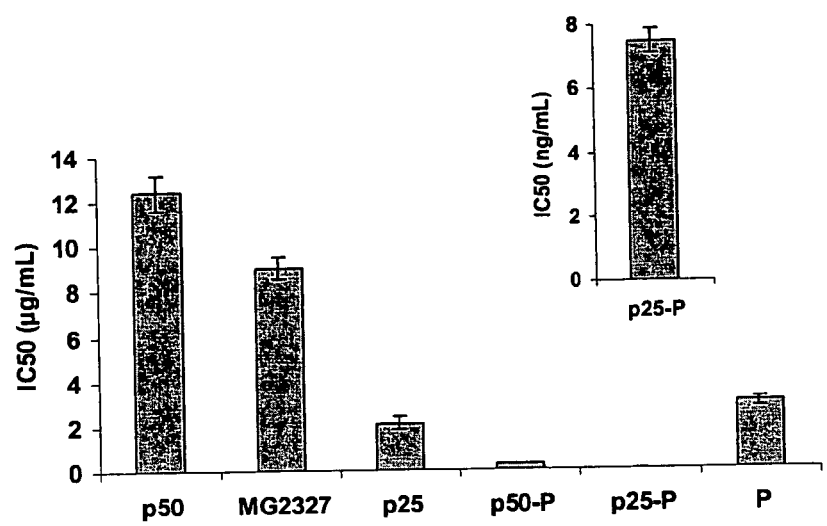

In order to demonstrate the antitumoral activity of the MG2327 preparation BALB/c mice were challenged with an intraperitoneal inoculation of tumor cells CB Hep.1 of myeloid origin able to cause ascitic murine tumors (Fontirrochi, G., Dueñas, M., Fernández de Cossio, M. E., Fuentes, P., Pérez, M., Mainet, D., Ayala, M., Gavilondo, J. V. and Duarte, C. 1993. Biotecnol Aplic. 10: 24-30). After 10 days, mice were injected intraperitonealy with MG2327 preparation or PBS. The 60% of the animals treated with 1 mg/kg survived, while only the 25% of the control were alive 45 days after the beginning of the treatment (FIG. 8). Total tumoral regression was observed in the treated survivors, showing a healthy condition, while in the controls, the tumors progress forming big solid masses and mice showed a deterioration of the general condition.

BALB/c mice bearing tumors of myeloid origin treated with one dose of 1 mg/kg of weight of the MG2327 preparation survived with total regression. This same dose increases the survival with a significant reduction of tumor volume in BALB/c mice bearing a tumor originated by E6/E7 transformed fibroblast. MG2327 protect BALB/c mice from the implant of myeloid tumors.

The MG2327 preparation was obtained as a result of the optimization of the culture conditions to produce antiproliferative molecules. MG2327 preparation was obtained as result of the optimization of the culture conditions to produce anti-proliferative moleculas, which constituye one protector agent against the implant and development of maligns tumors, in this manner as inductor of the production of anti-proliferative, apoptotic y anti-angiogenic moleculas in normal and tumors cells, that could be used advantageous in the profilaxis and therapy of the cancer, moreover of other diseases related with this events. CMIB 4202 strain over-express solubles proteins in the range of 45-50 y 20-30 kDa (50 y 25 kDa by SDS-PAGE, with one determination coefficient of 0.984) the fraction of 25 KDa, name as p25, showed a dosis-dependiente potent anti-proliferative activity in the experiment perform with the HEp-2 cellular line incubate with EDTA, while that la 50 KDa fraction name as p50, non inhibit the growing. However, to incubate p50 fraction within 5 µM $Zn_2SO_4$ showed anti-proliferative activity, but less than potent that p25 fraction. The $IC_{50}$ of the p25 and p50 fractions were 0.48 nM y 16 nM, respectively.

The isolated of proteic biomolecules with anti-proliferative effect (polipeptides and prodigiosin) was performed in the present invention, by only one chromatografic step: ionic interchange using a discontinue gradient of NaCl. It used one DEAE o QAE Sepharosa Fast Flow matriz, equilibrate with 50 mM of phosphate buffer, pH 8.00. The elution was performed with one discontinue gradient of NaCl: 50 mM of phosphate buffer –0.1 M NaCl, pH 8.00; 50 mM of phosphate buffer –0.2 M NaCl, pH 8.00; 50 mM –2 M NaCl, pH 8.00 and finally was elute the pigment fraction absorbed to the matrix a la matriz with absolute ethanol to 70%. The results confirm that proteic component preparation of 25 kDa have highest than capacity that proteic component of 50 kDa of the same preparation, to inhibit the growing of cells tumors, and both present in vitro biologic activity of independent form.

Fragments of several molecular size provoked the degradation of p50, that included fragments of 25 kDa. The increased of degradation of p50 was obtained with high temperature, and the generation of p25 was proportional with this increase of temperature, while that decreased the p50. The anti-p50 policlonals antibody, obtained in sheep, recognized to p25 in Western Blot assay, therefore the p25 fue originate as product of the degradation of the p50 protein. The products of degradation proporcionally increased with antiproliferative activity of products of degradation. This results confirm that the p50 autolisis is able of produce fragments of degradation with antiproliferative activity most potent that original molecule p50. Moreover the p25 protein also induce total regression of malign tumors of mieloide source. The fragments of p50 can be genetically conjugate, by some already known methodology of antibody fragments and generate inmunotoxins useful to treatment of proliferative etiology disease. Also this fragment alone or combined, with other proteic molecules maybe employe as carrier from inner of celulas orspecififc receptors. The fragment of p50 also can to expose itself to external medium of liberation system adjusted, to maintain a directional control from targets specific.

The proteolitic activity of p50 was inhibit with 7 mM de EDTA, and was demostrate that p50 is a metalloprotease, identified to mass spectrometer, belonging to Serralisins family.

The major similarity was founded in species with identifier PRZN_SERSP and PRZN_SERMA in the data base of Swis-sprot proteins. p25 protein purify by chromatography non present enzymatic activity and this correspond with the non catalytic of Serralisins carboxyl-terminal region The proteic components and the prodigiosin was formulated in one same composition that increased significantly ($p<0.005$), the inhibitory effect with respect to independent form of it formulation. The compositions were obtained maintaining the same relation of proteins and prodigiosin that employee to evalued the component of independent form. In such composition the s la prodigiosin can be found to concentration of 0.1-100 nM puede encontrarse a una concentración de, and the Serralisin fragments between 0.1-150 µg/mL.

Obtention of the composition that containing polipeptidics fragments derivated of the Serralisinas, with increased anti-proliferative effect, with respect to Serralisins integral moleculas, and the Serralisins-Prodigiosinas fragments combination which selectively potent biological activity of the composition.

Adicionally, these polipeptidic fragments have apoptotic effect over cancerigenas celulas. This apoptotic effect involved to mitochondrias, microtubules and DNA, fragmentation amplifying to program celular death signal, used losses doses of this compoisition. This events also were observed with combinated composition of polypeptide and prodigiosin.

Anti-angiogenic effect of MG2327 and anti-proliferative polypeptides fragments were evaluate by the method of formation of tubular structure in matrigel. Non citotoxic concentration of MG2327 and their fraction p25 y p50 were incubed with human microvasculature endothelial celulas (HMEC). The final result it evalued considering the tubular structure length formed and the number of interconexión between them. For this used Pro Express 4.5 Image-program. The result confirm that the treatment with MG2327 composition explain that treatment with protein and their antiproliferative polypeptides inhibit of form significative ($p<0.05$, ANOVA), the differentiation or maduration de la endothelial celula, demonstrating that MG2327, thus as their polipeptides isolated have anti-angiogenic activity.

Apoptotic, anti-angiogenic activity and the selectivity maintain one of them characteristic most important of the object composition of this invention, by it potential therapeutic and protector against the cancer.

The combination of fragments Serralisins and prodigisins family was demonstrated that are most potent and selective that of form independent as cancerigens. These polypeptides can be used in the obtention of recombinat toxins and immunotoxins to the profilaxis and cancer therapies, or others diseases related with proliferation of endothelial and transformed celulas.

These polipeptides and it possible combination with prodigiosins are son applied to pharrmaceutica industry to obtention of vacunales preparados, terapeutics or diagnostic of use human or animal against cancer and other patologies of kind proliferative that are highly selective and them have one ample espectrum of action.

FIGURE DESCRIPTION

FIG. 1. The interaction of S. marcescens with tumoral cells CB Hep.1 generates bacterial strains with high antiproliferative capacity and with modified protein expression. A—Cell survival. After 72 hours, cell survival was estimated by the MTT method. The strain CMIB 4202 showed a strong antiproliferative effect on the human tumoral cells HEp-2, while the effect of the SM1995 strain was very weak. These results were the average of tree independent experiments using four replics per sample. B—SDS-PAGE electrophoresis (silver stainning). CMIB 4202 over-expressed soluble proteins migrating around 25 and kDa.

Figure 2:
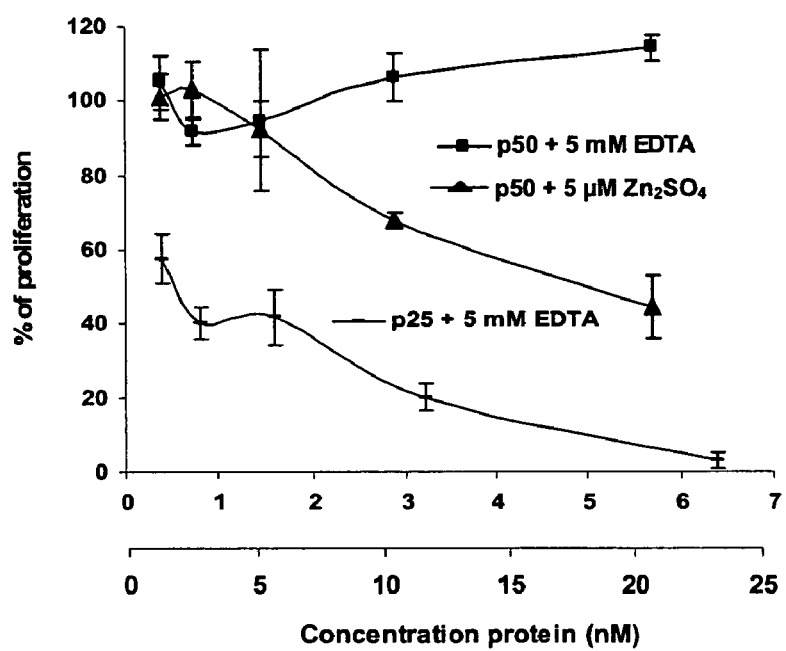

FIG. 2. Antiproliferative activity of the 25 and 50 kDa fractions on the cell line HEp-2. Cell viability was determined by the MTT method and expressed in percents respect to the control cells. The fractions were recovered from SDS gels (stained with zinc-imidazol) and renaturalized. The fraction around 25 kDa showed a strong antiproliferative activity ($IC_{50}$ 0.35 nM/mL), while p50 was unable to inhibit the growth. When $Zn_4SO_2$ 5 µM was added to the p50, an increase in the antiproliferative activity was observed ($IC_{50}$ 45 nM/mL) although inferior to that of the p25. The curves were generated from the mean values of five independent experiments and are plotted with the correspondent standard deviation (SD).

Figure 3:
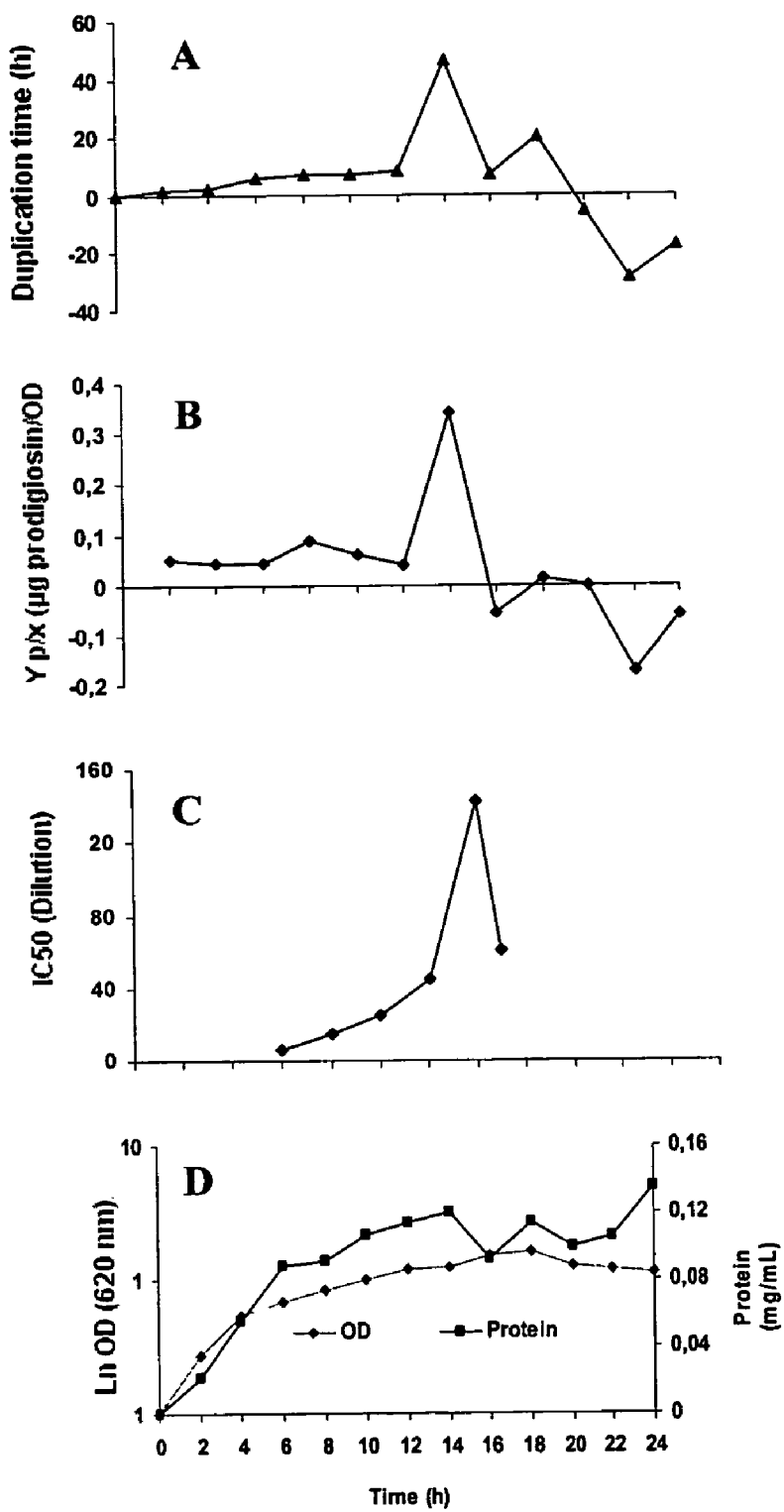

FIG. 3. Kinetics of protein and prodigiosine expression by the strain CBMI 4202. The expression of prodigiosins to the culture media occurs during the transition period from the growing phase to the stationary phase, where CBMI 4202 reach its higher duplication time. A—Kinetics of the cell duplication time. B—Efficiency of the prodigiosine expression (product/biomass). C—Kinetics of the anti-proliferative effect on Hep-2 cells, determined by the MTT method. D—Kinetics of the cellular growth determined by optical density and protein biosinthesis.

Figure 4:
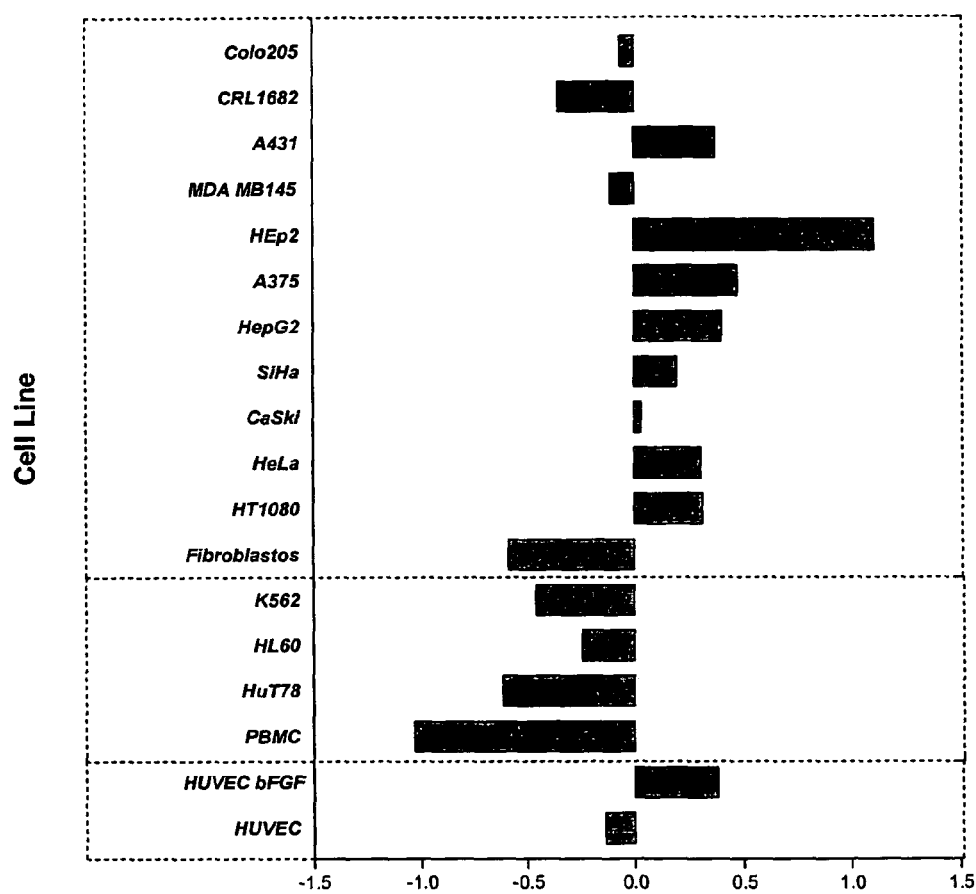

FIG. 4. Sensibility of tumoral and normal human cells to the treatment with MG2327. The normal cells have low sensitivity and those of haematopoyetic origin are less sensitive than the rest of the analized cell lines. Meanwhile cells activated for growing (HUVEC bFGF) and cells derived from tumoral malignant lessions are more sensitives.

Figure 5:
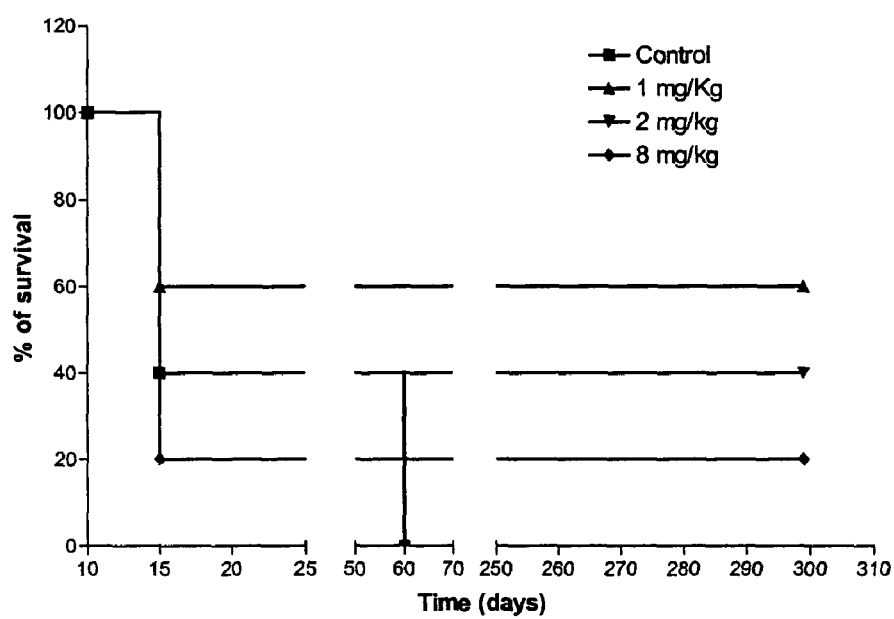

FIG. 5. Analyses of BALB/c mice survival after been treated or not with MG2327 preparation and challenged with the CBHep1 tumor. A—The dosis of 1 mg/kg induced a tumor regression in the 60% of the treated animals, while 100% of nontreated animals died by day 60. B—forty five days after tumor cells inoculation, non-treated animals showed an extremely weaken status, with the presence of solid tumors and acitis, while those treated with 1 mg/kg do not displayed evidences of tumors and survived for more than 300 days.

Figure 6:
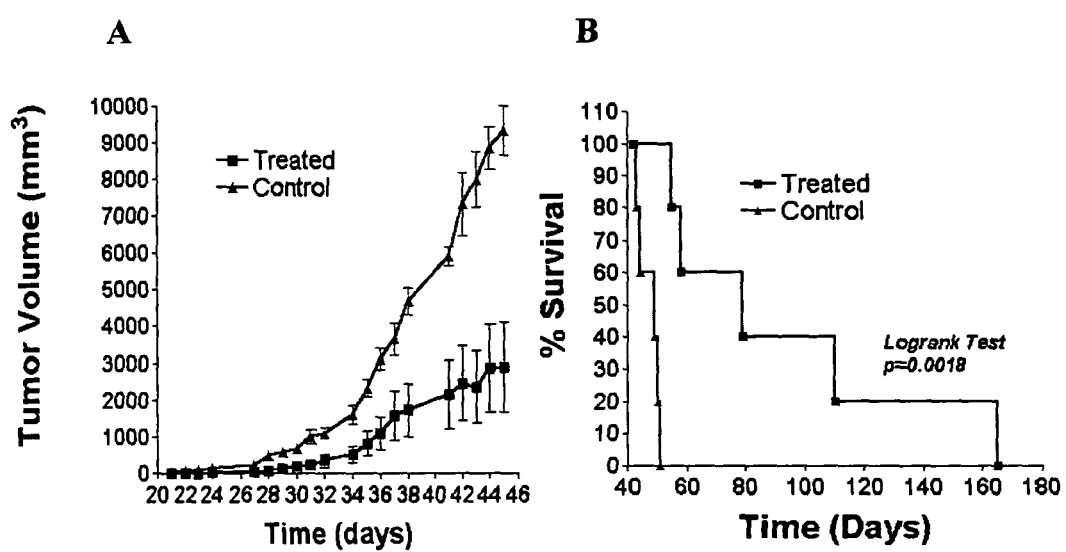

FIG. 6. Antitumoral effect of MG2327 on the tumoral model 3T316. A—The plot of the day to day mean for each group, reveal statistically significant differences among the tumoral volumes of treated and non-treated animals ($p<0.003$). The analysis of tumor growth trough the time evidence no significant variations ($p=0.109$) for the group treated with MG2327, while the negative control group showed a significant increase in this parameter ($p=0.04$). B—Survival pof treated and non-treated animals.

Figure 7:
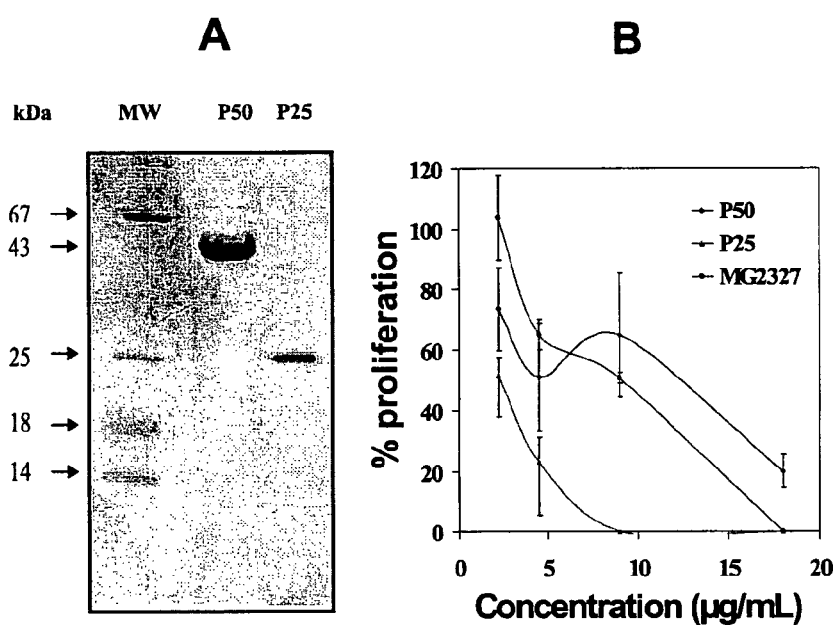

FIG. 7. Isolation of the proteic active principles from MG2327. (A) Electroforesis in SDS-PAGE (12.5%). Results of coomassie staining. Lane 1 shows the sample corresponding to the elution with 0.2 M NaCL, pH 8.00, where a proteic band corresponding to 50 kDa can be appreciated. Lane 2 shows a proteic band at 25 kDa. The staining was performed by the coomasie method. (B) Anti-proliferative effect on HEp-2 of p50 and p25 proteins on human tumoral cells. Dose-response relation to p25, p50 and MG2327 expressed in terms of total protein concentration.

FIG. 8. Antiporliferative effects of the active principles isolated from MG2327 on HEp-2 cells. The 50 and 25 kDa proteins enclosed in MG2327 showed a growth inhibition activity. The combination of these proteins with prodigiosins reduced the dose able to inhibit the growth of the 50% of the tumoral cells as compared to control ($IC_{50}$).

Figure 9:
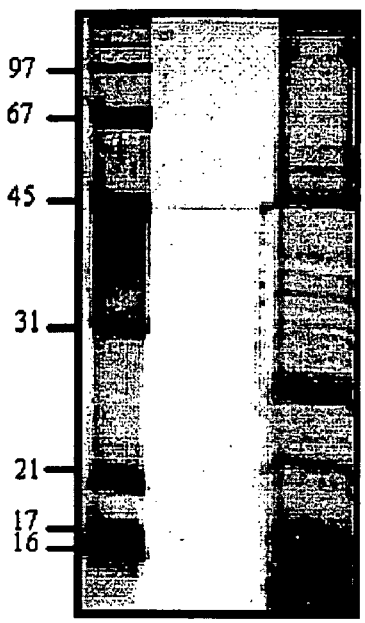
Figure 9:
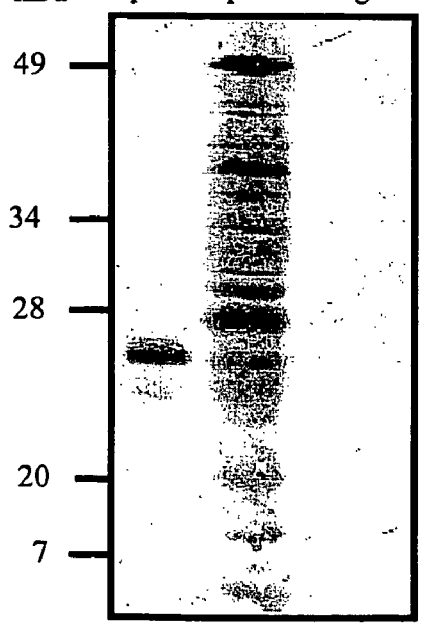

FIG. 9. SDS-PAGE and Western Blot. (A) Pattern of protein obtained from MG2327. The sample was analyzed by an SDS-PAGE gel (12%) and silver stained. (B) The proteic bands of approximately 50 and 25 kDa (arrows) were cut from a similar gel stained with a zinc-imidazole, renaturalized and re-run in a new SDS-PAGE. This was transferred to a nitrocellulose membrane and the western blot was developed with an anti-p50 antibody. The polyclonal antibodies obtained in goat were able to recognize the p25 and the degradations of the p50 and do not recognize the non related protein bands (Neg C).

Figure 10:
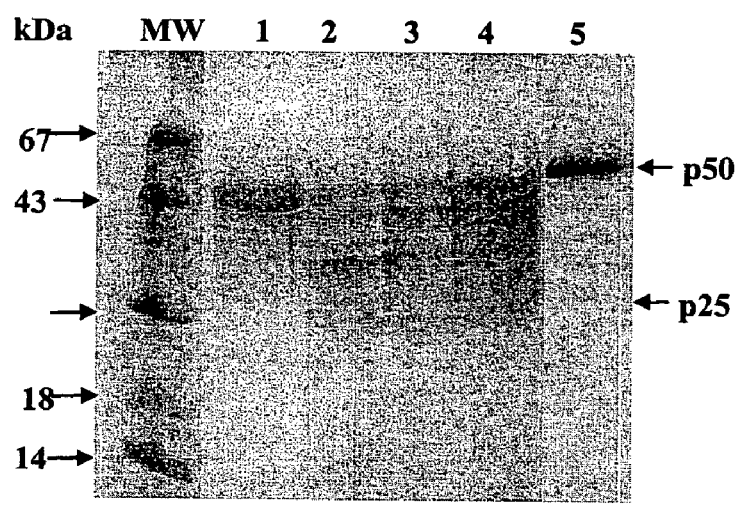
Figure 10:
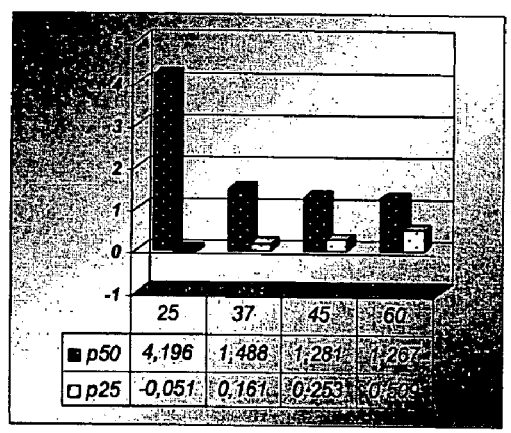

FIG. 10. p50 autolysis. A—SDS PAGE electrophoresis: 1-24° C., 2-37° C., 3-45° C., 4-60° C., 5-4° C. B—The densitometric anlyze of the p50 and p25 showed that with the increase in the temperature of incubation the intensity of the p50 band is decreased while the intensity of p25 band is increased.

Figure 11:
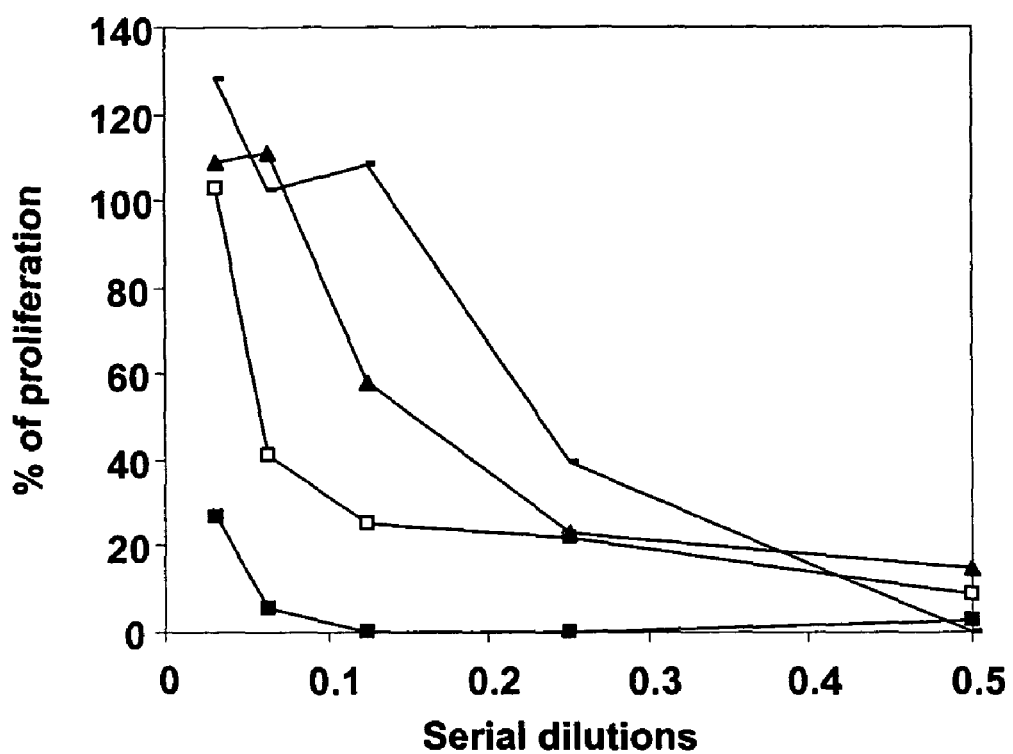

FIG. 11. p50 purified by DEAE Sepharosa Fast Flow chromatography. The P50 (eluted with 0.2 M NaCl), generated degradations with higher antiproliferative activity than the parental molecule.

Figure 12:
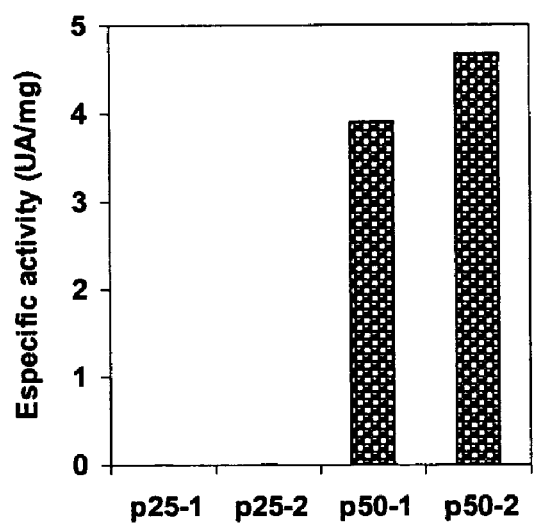
Figure 12:
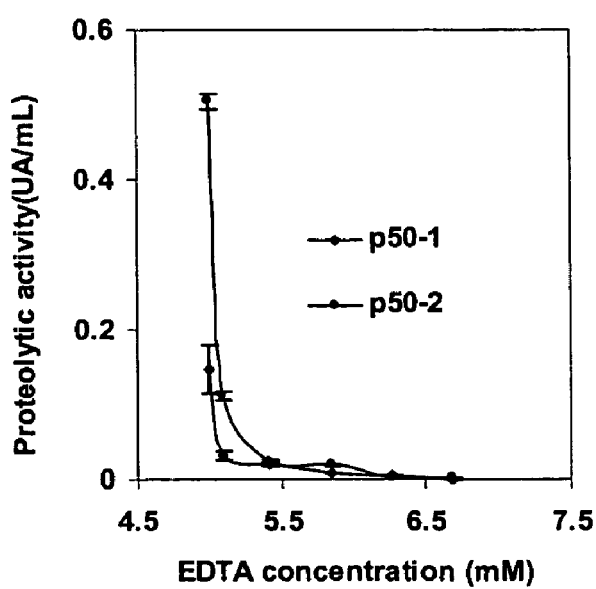

FIG. 12. Enzymatic activity of p25 and p50 obtained from different chromatographies. A—p25 do not present activity, while p50 showed enzymatic activity. B—The enzymatic activity of p50 was totally inhibited with 7 mM of EDTA.

Figure 13:
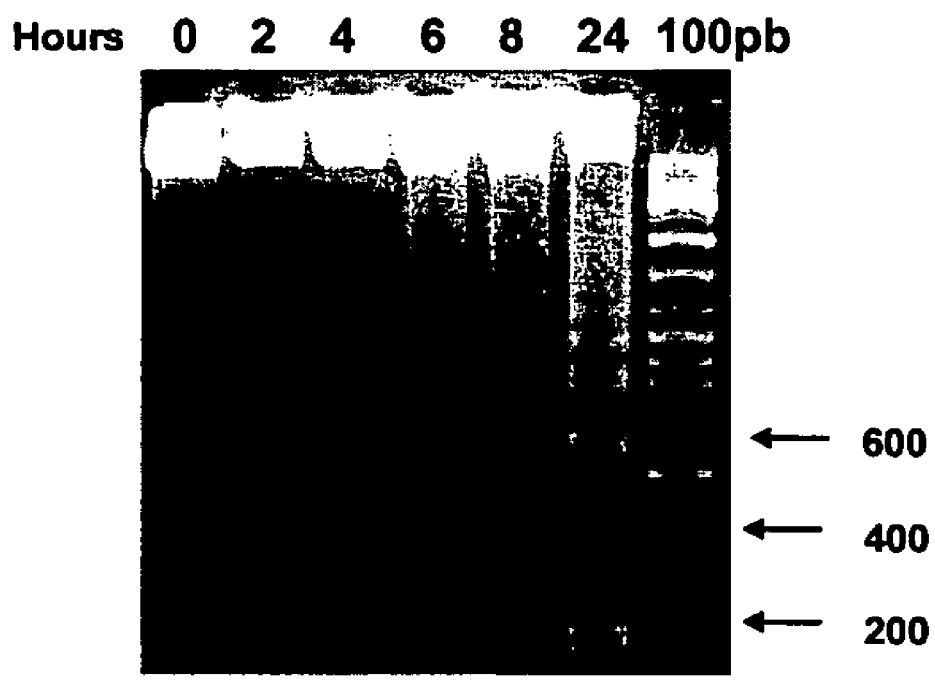

FIG. 13. MG2327 induced the time-dependent DNA fragmentation of the tumoral cells P3X63Ag8. Since the 6 hours of incubation the oligonucleosomal fragments can be observed and they increase with time, reaching the typical poptotic pattern with oligonucleosomal fragments of 180-200 base pairs at 24 hours.

Figure 14:
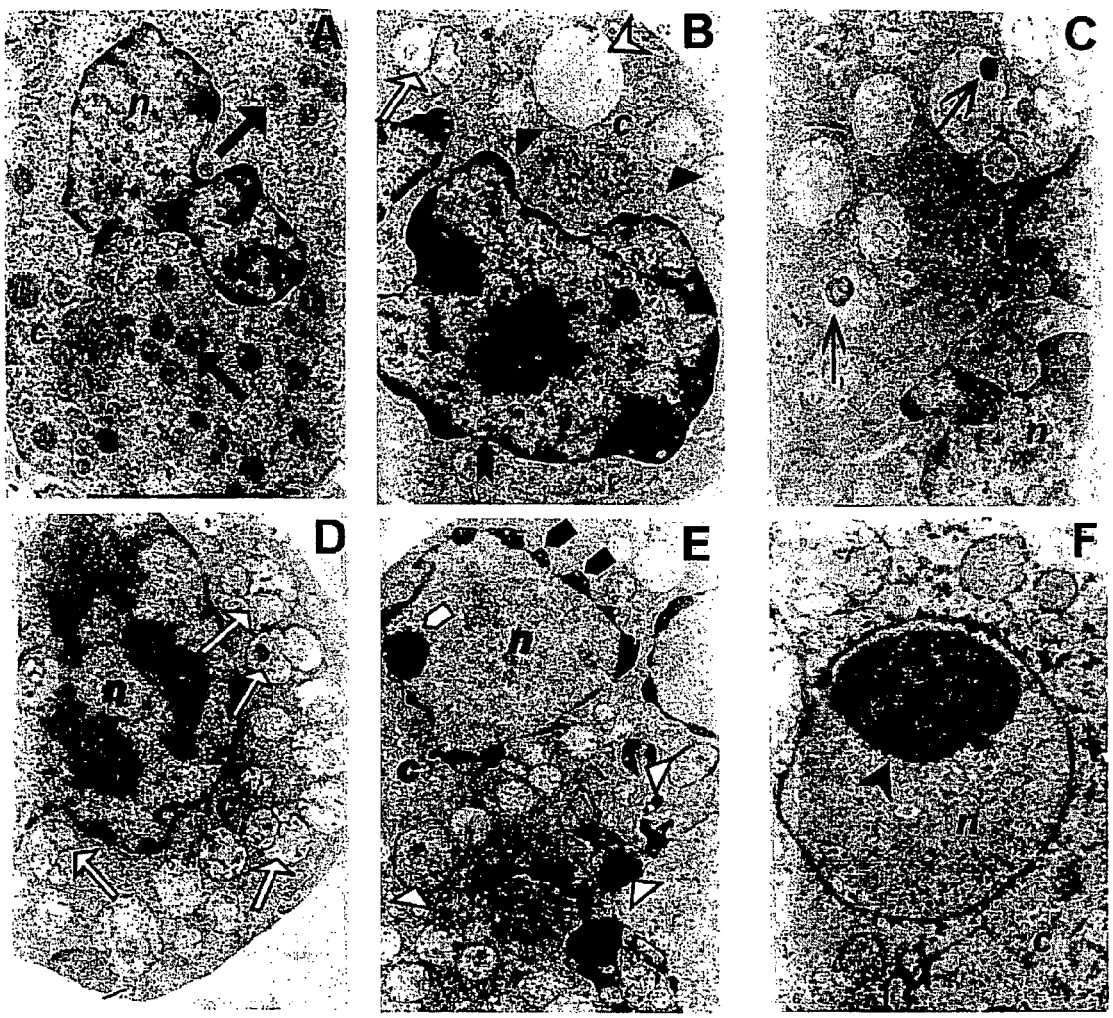

FIG. 14. FIG. 2 Ultrastructure of P3X63AG8 murine myeloma cells treated and untreated (control cells) with MG preparation at 22 µg/ml. (A) Electron micrograph of control P3X63Ag8 mieloma murine cells showed cytoplasm and nucleus of theses cells showed ultrastructure typical for normal cells and mitochondrial ultrastructure typical for normal cells: mitochondrial matrix had a higher density than the surrounding cytoplasm (↑). (B) Vacuolized bodies (which in part derive from altered mitochondria (▲)), mitochondrial swelling and disruption of cristae were present in the cytoplasm (▲), with normal nucleus (●) at 2 h after MG treatment. (C, D) Mitochondrial clustering and individual cristae become fused (↑), also observed after 2 hours of treatment in (B). (E) Electron micrographs with apoptotic morphology: condensation (●), margination and fragmentation of chromatin (●), and apoptotic bodies (Δ) at 6 h after MG2327 treatment. (F) Apoptosis revealed by compacted chromatin, the nucleus showed peripheral patches of condensed chromatin. {Note mitochondrial swelling and disruption of cristae, whole cytoplasm membranes were present on all time different}. Magnifications: ×6000 (E), ×10 000 (A, B, D), 15 000 (C) and ×40 000 (F).

Figure 15:
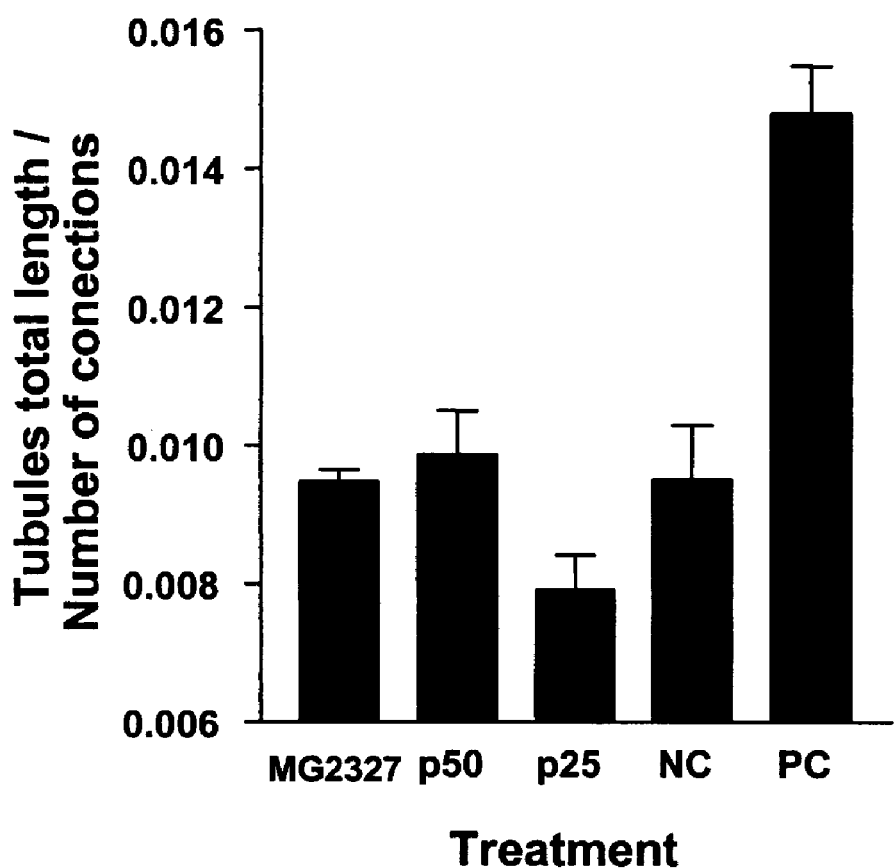

FIG. 15. Effect of MG2327, p25 and p50 (purified by chromatography) and their fractions on the differentiation of endothelial cells in Matrigel. HMEC cells were cultured in activation conditions (10 ng/mL EGF, 1 μg/mL of hydrocortisone) in the presence of similar concentrations of MG2327 (A), p50 (B) and p25 (C), no treatment (E) and without activation (D). In the graph (F) the results of 3 independent experiments are grouped, showing the inhibitory activity of MG2327 and its components on the formation of tubular nets in matrigel. Both MG2327 and p50 completely revert the activation induced to the level of non-activated cells (ANOVA MG2327, p50 and CN p>0.05. The cells treated with p25 showed an index of net formation inferior to that observed for MG2327 and p50 (unpaired t p=0.0107 and p=0.0498, respectively).

Figure 16:
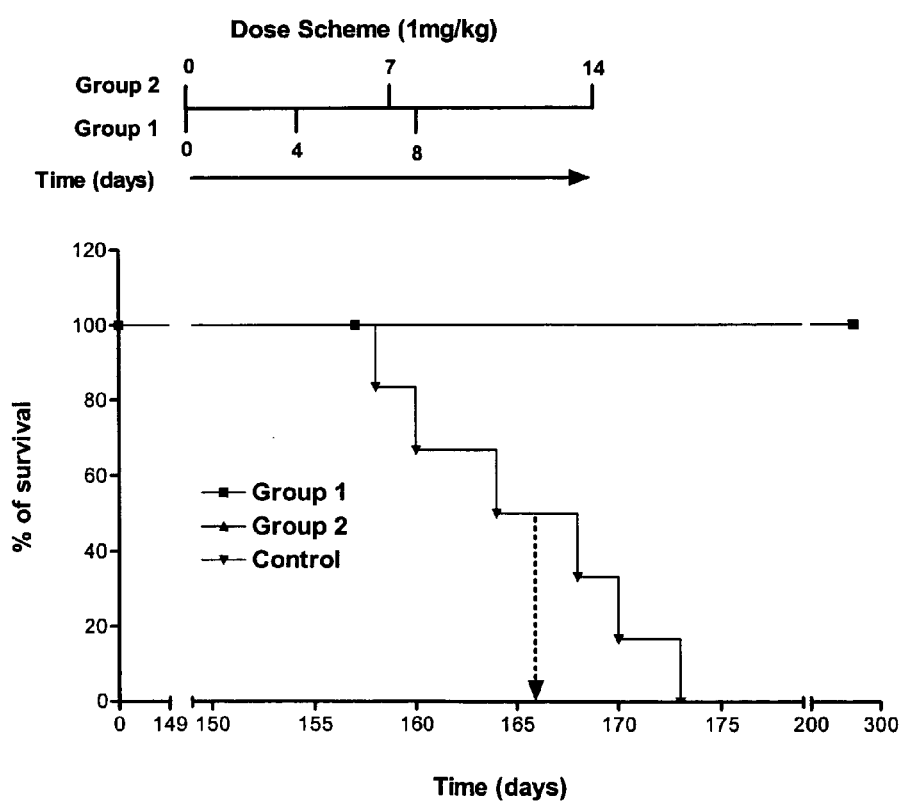

FIG. 16. Survival of BALB/c immunized or not with MG2327 and challenge with X63 myeloma cells. Using 3 and 6 doses of 1 mg/kg of MG2327 the 100% of the immunized animals reject the myeloid tumor.

EXAMPLES

Example 1

Obtention of the Strain CMIB 4202

In order to obtain bacterial strains producers of antitumoral molecules, the wild type Serratia Marcescens SM1995 isolated from the ventral surface of BALB/c mice was mixtured with the tumoral cells CBHEp.1 (Alemán, M. R., Valdés, R., Pérez, M., Ibarra, N., Reyes, B., González, M., Mendoza, O., Padilla, S., Agráz, A. and Rodríguez, M. P. 2000. Biopharm 13:48-52) and were inoculated intraperitonelly in BALB/c mice, previously inoculated 10 days before with heavy liquid petrolate. Eigth days after the inoculation of the cells mixtures, ascitic extractions were performed every 2 days. The kinetics of tumor growth was analyzed and the microbiologycal control was performed to the ascitis of each animal presenting tumor regression.

The isolated bacteria were grown in different media and culture conditions. The culture supernatants were steril filtered using membrane filters of 0.22 μm and their toxicity was evaluated on CBHEp.1 cells. The strain with higher cytotoxicity was deposited with the accession number CMIB4202 in the Collection of Microorganism with Biotechnological Importance of the Center of Genetic Engineering and Biotechnology, Habana city, Cuba. CMIB4202 and its parental strain SM1995, were cultured in parallel in 5 L fermenters, in peptone-glycerol media at 28° C. The steril filtrate of CMIB 4202 evidence a dose dependent activity while the one from SM1995 has only a little activity on the human cancer cell line HEp-2 (FIG. 1A) in the anti-prolifferative assay using the MTT method (Skehan, P., Storeng, R., Scudiero, D., Monks, A., Mcmahon, J., Vistica, D., Warren, J. T., Bokesch, H., Kenney, S. and Boyd, M. R. 1990. J. Natl. Cancer. Inst. 82:1107).

The strain CMIB 4202 over-expressed soluble proteins in the ranges of 45-50 y 20-30 kDa (50 y 25 kDa as determined by SDS-PAGE, with a coefficient of determination of 0.984), FIG. 1B.

The p25 fraction recovered from the bands presented in SDS gels stained with zinc-imidazole (Hardy, E., Santana, H., Sosa, A., Hernández, L., Fernández-Padrón, C. and Castellanos-Serra, L. 1996. Analytical Biochemistry. 240:150) showed a strong antiproliferative dose dependent activity in HEp-2, while the p50 fraction do not inhibit the cell growth. Nevertheless, when p50 was incubated with 5 μM $Zn_2SO_4$ showed antiproliferative activity but lower as the observed for p25 (FIG. 2). The $IC_{50}$ of the fractions p25 and p50 were 0.48 nM and 16 nM, respectively.

With the objective of compare the ability of both strains to express the proteins, a factorial ANOVA was applied. The value of the probability of interaction was not significant (p=0.93).

On the other hand, the probability of both main effects showed that both proteins are expressed in different amount significantly (P=0.01) and that this amount is highly strain depended (P=0.0004). Furthermore, there were significant differences in expression for these proteins between both strains (P<0.001).

Example 2

Obtention of the MG2327 Anti-Proliferative Preparation

For obtained one anti-proliferative preparation to part of CMIB 4202 S. marcensces strain, was produced 1 L of culture of microorganism and media of culture optimal to produce molecules of interest (FIG. 3). CMIB 4202 culture was centrifuged to 12 000 g y 4° C. by 30 minutes. Sobrenatan was colected and subsequently filtrate by molecular tamizaje from 0.2μ under esterility condition. The volumen of the sobrenadante was reduce 10 times in the same condition of esterility. The volumen of the supernatant was 10 times reduced used a membrane of 10 kDa exclusion limite and dialyzed against PBS to 4° C. during 24 h, in physiological condition. Material dializaded was filtrate in esteriles condicions, and were dispènsed in vial og 5 mL fueron dispensados en de apirogenics cristal viales. The preparation was stored to 4° La preparación fue almacenada a 4° C. and name MG2327.

The climbed to fermentator of 5 L was realize with conditions already established in screen: peptone-glicerol media to 28° C. by 14 h, areacion 1 vvm, 250 rpm y 0.1 of optic density inicial. The media culture was ajust to pH physiologic, and the fermentación was to pH free The rest pase was realized the same form that in scree.

Example 3

Characterization of the Antiproliferative Activity of the MG2327 Preparation "In Vitro"

For the characterization of the antiproliferative activity of MG2327 "in vitro" a panel of human cell lines was evaluated (table 1). A total of 2000 cells, except for PBMC (20000), were seeded in 96 wells culture wells, and different concentrations of MG2327 were added. After 72 hours, the number of survival cells was estimated by addition of MTT (Skehan, P., Storeng, R., Scudiero, D., Monks, A., Mcmahon, J., Vistica, D., Warren, J. T., Bokesch, H., Kenney, S. and BOYD, M. R. 1990. J Natl Cancer Inst. 82:1107). The soluble formazan products were detected at 540 nm in a multiscan plate reader. MG2327 showed a wide range of cytotoxic activity against the analyzed human cell lines. The IC50 was in the μg/mL range.

TABLE 1

Cells and culture media used on the "in vitro" study

| | | |
|---|---|---|
| FIBHUM | HUMAN FORESKIN DERIVED FIBROBLAST, P 3-6 | DMEM, 15% FBS*, INSULIN 30 µG/ML |
| H82 | Human lung carcinoma | RPMI 1640, 10% FBS |
| MDA-MB145S | Breast human adenocarcinoma | DMEM, 10% FBS |
| Colo-205 | Human colon carcinoma | RPMI 1640, 10% FBS |
| HT1080 | Human fibrosarcoma | DMEM, 10% FBS |
| Hela | Human cervical carcinoma | DMEM, 10% FBS |
| HEp-2 | Human laryngeal carcinoma | MEM, 10% FBS |
| HepG2 | Human hepatocarcinoma | DMEM, 10% FBS |
| A375 | Human melanoma | DMEM, 10% FBS |
| PBMC | Human Peripheral mononuclear cells | RPMI 1640, 10% FBS, IL-2 |
| HuT78 | Human Cutaneous T cell lymphoma | RPMI 1640, 10% FBS |
| HL60 | Human promyelocytic leukemya | RPMI 1640, 10% FBS |
| K562 | Human eritroleukemya | RPMI 1640, 10% FBS |
| CRL 1682 | Human pancreas adenocarcinoma | RPMI 1640, 10% FBS |
| A 431 | Human vulvar adenocarcinoma | RPMI 1640, 10% FBS |
| SiHa | Human cervical carcinoma | RPMI 1640, 10% FBS |
| CaSki | Human cervical carcinoma | RPMI 1640, 10% FBS |
| HUVEC | Human vascular endothelial cells | M199 30% FBS 10 ng/mL bFGF |

*FBS: Fetal Bovine Serum

MG2327 selectivity was compared to the commertial drug Doxorrubicine (DXR) using the HT1080 cell line (from a fibrosarcoma) and primary fibroblasts. The antiproliferative assay used was described above. Serial dilutions of DXR and of the MG2327 preparation were applied from 10 µg/mL and a five point curve was generated. The mortality ratio was calculated for each point as the relation between the mortality percent for HT1080 and the mortality percent for the primary fibroblasts. The higher differences were detected at the lower concentrations tested (MG2327 9:1, DXR 1.7:1). MG2327 was very selective at concentrations below 2 µg/mL.

HEp-2 cells originated from a laryngeal carcinoma are very resistance to the antitumorals used in clinic as compared to the other cell lines analyzed. For this reason, we used it as a model for the "in vitro" studies of the effects of the MG2327 preparation. A comparison of the cytotoxicity curves generated for HEp-2 cells treated with known antitumoral drugs, showed similar results (40%) of proliferation at 3 µg/mL for MG2327 preparation, Cisplatin (CDDP), Doxorubicine (DXR), Vincristine (VC), Vinvlastine (VB) and Taxol (TX) ($p>0.05$, test de ANOVA). In the same conditions other antitumorals like Ara C, Metotrexate (MTC), Bleomicine (Bleo) y Ciclophosfamide (CPA), do not showed effect. CDDP is one of the antitumorals authorized by the FDA for the treatment of laryngeal cancer, and the analysis of the survival curves for MG2327 preparation and CDDP showed similar values for the IC10, $IC_{50}$ and $IC_{90}$.

The sensibility study of the different cancerigenas cellular lines o non cancerigenas (FIG. 4) showed that normal cellular lines are little sensity to, whyle that melanoma, carcinoma laringeo, fibrosarcoma, hepatocarcinoma, y carcinomas Cervico-uterinos (carrier of the virus of the humano papiloma virus), are very sensity. The carcinomas of de origen hematopoyetic source are less sensity. The celulas HUVEC activity to it growing are most sensity to the MG2327preparation that the non activates The result previous showed that the preparation MG2327 have ample espectrum of citotoxic action over malign celulas lines, with selective effect with effect on tumors/transformed and activate celulas to it growing.

Example 4

Antitumor Activity of the MG2327 Preparation

To demonstrate the antitumoral activity of the MG2327 preparation we employed BALB/c mice, that were implanted intraperitoneally (i.p.) with CB Hep.1 tumor cells, of myeloid origin, able to give rise to murine ascitic tumors (Fontirrochi, G., Dueñas, M., Fernández de Cossio, M. E., Fuentes, P., Pérez, M., Mainet, D., Ayala, M., Gavilondo, J. V. and Duarte, C. 1993. Biotecnol Aplic. 10: 24-30). After 10 days, mice were injected i.p. with MG2327 or PBS. Sixty percent of the animals treated with 1 mg/kg of weight survived, while only 25 percent of the controls lived to 45 days after initiated treatment (FIG. 5). Total tumor regression was observed in all treated surviving animals, that showed a healthy state, while in the controls the tumors progressed forming large solid masses, and the animals exhibited a unhealthy general state.

BALB/c mice bearing a tumor of fibroblasts transformed with E6/E7 increased their survival after being treated with the MG2327 preparation, showing a significant reduction of tumor volume.

Also, to evaluate the antitumoral activity of MG232, a model of cancer associated to the human papilloma virus (HPV16) developed by Hernández et al. (Hernández, P., Merina, N., López-Ocejo, O. and Araña, M. J. 2000. Biochem Biophys Res Commun. 270:119-124) was used. Two groups of BALB/c mice were inoculated subcutaneously (s.c.) with $2\times10^6$ 3T316 cells in the left ventral zone. After 48 hours, a dose of 0.75 mg/kg of weight of MG2327 or PBS was ministered s.c., near the primary cell inoculation in the control group, daily measurements were done with a caliper. The tumor volume was calculated using the standard formula $V=0.52\times a^2\times b$, where a is width and b is the length of the horizontal perimeter of the tumor (Hernández, P., Merina, N., López-Ocejo, O. and Araña, M. J. 2000. Biochem Biophys Res Commun. 270:119-124). Behavior is shown in FIG. 6.

The differences in the time of tumor development were statiscally significant ($p=0.0054$) between the treated and non-treated animals. The study of the relationship time:treatment with the ANOVA test showed that the same magnitude of difference doesn't maintain between the treated and non treated groups; this indicated the existence of a difference related to the treatment applied to the animals.

When a Wilcoxon test was applied for the paired data to the measurements between days 21 and 45 of each group, we detected a significant increase of tumor volume for the control group ($p=0.043$), not being this the case for the treated group (FIG. 6A). To analyze the existence of significant differences between the groups in each moment of evaluation, we applied a Mann-Whitney U test that detected significant differences, exception made of the first point (p<0.01). Also, we detected an important difference in the speed of growth of the tumor. The growth curves were adjusted to one line, and the slopes were calculated from the equation generated by the best fit. The slope comparison indicated that the tumor in the control group grew at a speed significantly higher that the observed for the treated group (p=0.0088).

The mice of the control group died between days 45 and 64 due to the tumor implantation, while the animals in the treated group started to die in day 52, with a 20% survival that maintained in time (170 days), FIG. 6B.

Adjusting the survival data to a Bayesian hierarchy model (Weibull regression with 500 iterations) we obtained a statistically significant difference (p=0.02447), that was confirmed when it was shown that the confidence intervals for the average survival time were totally exclusive.

Example 5

Fraction of the MG2327 Prepation. Isolated of the Non Proteic Biomolecules

For determined the composition of the MG2327 preparation was perform their molecular fraction and was evalued their capacity to inhibit in vitro the cellular growth of the Hep-2 human tumor cellular line.

The polissacaride fraction (tr=6.85 min) was separated in Aminex gel HPX 87-N chromatography (dimensiones: 300× 7.8 mm, flujo: 0.5 ml/min). Was utilized patterns of fructose tr=13.15 min., glucose tr=12.12 min., dissacaride tr=9.40 min., trissacaride tr=8.24 min., polissacaride tr=7.01 min. The pigment fraction was separated mediated a butilo TSK column of the MERCK equilibrated with phosphate 20 mM, pH=7, where remain retained into matriz, subsequently was elute employment absolute ethanol. Abssortion spectrum (ethanol 100% a pH 5.00) of the product obtained showed a band with maximum 470 y 490 nm and a maximum peak in 537 nm, that correspond with characteristic describe of the monomers and dimer of the, respectively, with reported anti-proliferative activity (Pérez-Tomas, R. and Montaner, B. 2003 Histol. Histopathol. 18: 379-385; Montaner, B., and Pérez Thomas, R. 2003. Curr Cancer Drug Targets. 3:57-65). The polissacaride isolated non showed inhibit effect, while that fraction correspond to prodigiosin showed dose-dependent anti-proliferative activity.

Example 6

Fraction of the MG2327 Preparation. Isolated of the Proteic Biomolecules with Antiproliferative-Effect, Mediate Only One Chromatography Step: Ionic Interchange with NaCl Discontinued Gradient. Composition MG2327 preparation was applied to a DEAE Sepharose Fast Flow matriz, equilibrate with 50 mM de buffer phosphate, pH 8.00. The elution was perform with a NaCl discontinued gradient: 50 mM of buffer phosphate-0.1 M NaCl, pH 8.00; 50 mM of buffer phosphate-0.2 M NaCl, pH 8.00; 50 mM of buffer phosphate-2 M NaCl, pH 8.00 and finally was elute the absorbed pigment fraction to matriz with 70% absolute ethanol The fraction correspond to 0.2 M NaCl, pH 8.00 and the first elute colected of the fraction that the no stick (pass), showed dose-dependent anti-proliferative activity in the test already described. SDS-PAGE electrophoresis was observed a protein band to height of 50 kDa and a maximum band (pureza>90%) to height of 25 kDa, respectively (FIG. 7A). The molecular weight were calculated mediated the function that relate the molecular weight of the commercial pattern with the distance of migration of the bands; $r^2$=0.984.

The FIG. 7B. Show the anti-proliferative effect of p50 y p25 compared with the MG2327 preparation. The p50 y la p25 showed anti-proliferative effect on HEp.2.

The Table 2 show the compared results between p50, p25 and the MG2327 preparation, employing the estatistical analysis of varianza (ANOVA). It performed a comparation of the respons to every employed doses. It may observe that exist significative differences between the activities of the three analyzed sample. These difference depend of the employed doses. To high concentration of the components of the preparation (9 y 18 μg/mL) existence significative differences between the fraction of 25 y 50 kDa, where the fraction of 25 kDa was most active, nor being in this manner to lower concentrations (2.25 y 4.5 μg/mL).

TABLE 2

Results comparatives between the proteic componentes and the MG2327 preparation, employing the estatistical analysis of varianza (ANOVA).

| Concentration (μg/mL) | ANOVA | | | |
| --- | --- | --- | --- | --- |
| | Inter-samples | 25-50 | 25-MG2327 | 50-MG2327 |
| 2.25 | 0.0110 | 0.0649 | 0.0089 | 0.0958 |
| 4.5 | 0.0316 | 0.0685 | 0.0081 | 0.3728 |
| 9 | 0.0040 | 0.0318 | 0.0151 | 0.4271 |
| 18 | 0.0015 | 0.0243 | 0.3206 | 0.0243 |

Between the proteic component of de 50 kDa and the MG2327 preparation was exist difference significatives to the dose of 18 μg/mL where the preparation was most active, obtaining the inhibition of the growing of 100% of the tumor cells, while that proteic component of 50 kDa gain to inhibit approximately the 80% of growing. To the doses of 2.25, 4.5, y 9 μg/mL nor was exist difference significatives between the respon provoking to the fraction of 50 kDa and the MG2327 preparation.

However, the activity of the proteic component of 25 kDa was significantly different to the of MG2327 preparation to the doses of 2.5, 4.5 y 9 μg/mL, where the proteic component of 25 kDa showed major biologic activity and to the doses of 18 μg/mL nor was exist significatives difference, already that both same gain inhibit the 100% of the tumors cells.

These results evidenced that proteic component of 25 kDa have major capacity to inhibit the growing of the tumors cells, that proteic component of 50 kDa and that both components showed biologic activity in vitro of independ manner.

these esquelu of purification was again three ones obtained homogeneous results.

Example 7

Composition of Polypeptide of Serralisin with Prodigiosin

It formulated the proteic components and the prodigiosin in one same composición that increase significantly (p<0.005) the inhibitory effect with respect to its effect of independent form in the FIG. 8 it graphical the $IC_{50}$ of the anti-proliferative biomolecule that isolated of the MG2327preparation and its compositions The MG2327preparation is referred to total protein. The composition was realized to remain firm the same relation of protein and prodigiosin that the employed when was evaluete the components of independent form. In such composition the prodigiosin can to encountert to one concentration of 0.1-100 nM, and the Serralisin fragments of 0.1-150 µg/mL.

Example 8 p50 Gender p25

Anti-p50 obtaining in sheep was utilized to know the relation between p25 y p50. MG2327 was to apply to SDS-PAGE gel al 12% and with a Imidazol-Zinc stanning (Hardy, E., Santana, H., Sosa, A., Hernández, L., Fernández-Padrón, C. and Castellanos-Serra, L. 1996. Analytical biochemistry. 240:150-152). Aproximately the proteins bands de 50 y 25 kDa, (FIG. 9) were cut, renaturalized in gel and applied to SDS-PAGE. These were transfer to nitroceluosa membrane and the Western Blot was to realize. The anti-p50 policlonal antibody recognized to p25 and degradation of p50 the sizes moleculares were estimated with marked of prestaining molecular weigh (Bio-Rad). The Western blot showed here is representative of three equals experiment Example 9

The Degradation of p50 Products Source to Temperature are Most Active that Itself p50

The p50 obtained in the example 6 was incube to a different temperature and its anti-proliferative activity was tested over HEp.2, used the MTT method already previously describe. The degradation pattern produced to everyone condition (4, 37, 45 y 60° C.) was cuantifique to densitometria.

The generation of fragment produce of the degradation was directly proportional with the increase of the temperature, therefore to when the amount of p50 decrease was increase the p25 as product of the degradation of p50 (FIG. 10). The products of the degradation of p50 showed major anti-proliferative activity that the origin p50 (FIG. 11).

Example 10 p25 Induce Regression of Malignant Tumors

The protein p25 obtained by the chromatography describe in the Example 6, was applied to revers phase chromatography of (RP-HPLC), to verify its homogeneousness and purity. It employed a gradient of acetonitrilo of 0-100 en 100 min. It observed a peak of proteins with purity major of the 90%, demostrated the homogeneity of the eluate purify.

The p25 was them injected i.p. to mice BALB/c after of 8 days of implanted P3X63Ag8 mieloide tumor and perfectly development. The doses of 22 µg/kg of weigh of p25 induced total regression in the 80% of the animals treatment. the negative controls death in the end of 30 days, where already had development compact tumors.

Example 11 p50 is a Metaloprotease, while that p25 no Have Proteolytic Activity

The modify method of Anson y Mirsky (Anson, M. L., Mirsky, A. E. 1932. J. Gen. Physiol. 16: 59) using casein as sustrate, was adjust in our laboratory with Tripsina ($y=1.9314x-0.682$; $R^2=0.999$). The proteic fraccions obtained in the chromatography describe in the Example 6 were assay with this method. P50 showed proteolytic activity that was inhibit with 7 mM de EDTA, therefore this result a metaloprotease. p25 no showed enzymatic activity, FIG. 12.

The method of the cimogeno using gelatine as sustrate (Vacca, A., Iurlaro, M., Ribatti, D., Minischetti, M., Nico, B., Ria, R., Pellegrino, A. and Dammacco, F. 1999. Blood. 94:4143-4155) was employed to verify the proteolytic activity of p50 and p25. Moreover was analized the enzymatic capacity of the degradation of p50. In this assay the protein p50 obtained by the chromatography describe in the Example 6 showed enzymatic activity. The proteic band fraction of the gel to the height of 25 kDa (from MG2327) showed proteolytic activity; whyle that p25 obtained by chromatography no showed this activity.

Example 12

Identification of Anti-Proliferative Polypeptides of 25 kDa from MG2327

To the identification of proteins with anti-proliferative activity present in the band of 25 kDa, was cleaved the SDS-PAGE gel (describe in the l Example 8) with MG2327 applied. The band was incubed during 5 min en 1 mL of Tris/HCl (100 mM pH 8.5) buffer until that had totally transluced. The band was cleaved in small cube of nearly 1 mm$^3$, absorbing with acetonitrilo, rehydrated in a smallest volume of bicarbonate of ammonium (25 mM) containing trypsin or LEP to a concentrattion of 12.5 ng/µL. The digestion in gel was incubed to 37° C. by 18 h in a thermostatic mingler The peptides resultants of the LEP digestion was analyzed by MALDI-MS. The monoisotopic ions of the signals most intense was introduced in the ProFound program to the identification of the interest protein in the secuency data base. Although we no performed none taxonomic restriction during the search in the data base, the 50 kDa protease of *Serratia marcescens* EC 3.4.24.40 was alienable as the of major similitude. Four peptides (51-57, 58-66, 67-80 and 81-90) ownership to the N-terminal region and one (402-409) ownership to C-terminal region of the protein. The molecular size EC 3.4.24.40 delay of the presents in the band analized (nearly 25 kDa, estimated by SDS-PAGE). These finding suggest that the band of 25 kDa contain two fragments co-migrate of 25 kDa with like to protein of 50 kDa EC 3.4.24.40 belonging to Serralisin family.

To confirm this hypotesis, was development of the 25 KDa band of the protein a tryptic digestion. The ESI-MS espectrum of the peptides removed was deconvolute and the signals most intensity were introduced in the Profound program. The way out showed the same protein previously identify (EC 3.4.24.40). The sequence cover of the tryptic digestion (21%) was major that the before digestion (10%). The sequence cover map proved seven peptides that que coincided very good with some of the tryptic fragments PRZN_SERMA/PRZN_SERSP of the proteins. Five of them (28-41, 58-66, 67-80, 81-90 and 163-171) corresponded to the N-terminal region, while that the remainder two peptide (351-373 and 374-393) correspond to the C-terminal region. These results not only corroborate the prior identification of the protein, but that the map cover suggest the presence of two co-migrates fragments of 25 kDa of the identify protein as PRZN_SERMA/PRZN_SERSP, in the analized band The ESI-MS/MS espectrum correspond to peptides of the N- y C-terminal regions of the previously mentioned proteins were explained handly and the parcials sequences were removed by its identification, Table 3.

TABLE 3

Interpretation manual of the ESI-MS/MS espectrum of five peptides presents in the 25 kDa band The peptides of the 1-4 ownership to the N-terminal region of the PRZN_SERMA/PRZN_SERSP proteins, whyle that 5 peptide correspond to the Ia C-terminal region of this same proteins.

| $m_1$ | Sequence Tag | $m_2$ | Peptide sequence | z | m/z expected | m/z theoretical | Error |
|---|---|---|---|---|---|---|---|
| 705.47 | AQENS (SEQ ID NO: 5) | 1235.74 | 28-41 | 2 | 792.91 | 792.89 | 0.02 |
| 522.28 | TFSF (SEQ ID NO: 6) | 1004.54 | 58-66 | 2 | 559.29 | 559.28 | 0.01 |
| 677.38 | AVN | 961.58 | 67-80 | 2 | 692.35 | 692.34 | 0.01 |
| 730.40 | EAS | 1017.58 | 81-90 | 2 | 582.79 | 582.79 | 0.00 |
| 1117.84 | GGFX (SEQ ID NO: 7) | 1493.08 | 351-373 | 2 | 1031.45 | 1031.48 | 0.03 |

The methods employed and results obtained we concluded that in the 25 kDa band analized exist one mixture of proteins that have fragments with similitude PRZN_SERMA/PRZN_SERSP of the proteins N and C-terminal.

Example 13

Identification of the p50

To identify the protein p50 with anti-proliferative activity, the proteic fraction correspond to the 50 kDa protein obtained of the protocol of purification describe in the Example 6, was digested with Lys-C endoproteinase. The identification of the peptides was performed by means of sequenciation by automatized Edman Degradacion and a JMS HX-110 doble sector masses spectrometer, with FAB cannon. These results and the aligned realized by el Swissprot and PIR software was concluded that such protein to means of to Serralisin's family with 50 kDa molecular weight. The major similitude was found to the species with PRZN_SERSP y PRZN_SERMA identificators in the Swissprot bank. The molecular mass of all peptides analized by mass spectrometer coincided with the expect teorics amount to peptides of these digesting proteins with Lys-C endoproteinase.

Example 14

Identification of the Purified p25 by Chromatography

To identify the 25 kDa protein with anti-proliferative, apoptotic and anti-angiogenic activity, the purified p25 by DEAE chromatography describe in the Example 6 was applied to SDS-PAGE. The proteína band was washed during five minutes with 500 μL of water, after was off colour with a citric acid solution 100 mM, subsequently was newly washed with MilliQ water, cut in small cube approximately of 1 mm³. After, it addition acetonitrilo until it's deshidratation and excess was eliminated. The gel cubes were dehydrated totally in a evaporative centrifuge and subsequently rehydrated in a ammonium bicarbonate solution (50 mM) that contained trypsin to a concentration of 12.5 ng/μL. After were incubed in a mingler thermostated during 30 minutes to 37° C. overnight The peptides were passively avoid to add 20 μL of an ammonium bicarbonate solution and additional incubation to 37° C. during 45 minutes. The peptides were removed by the use of ZipTip$_{C18}$™ and subsequently it acidulous the mixture reaction to add 5 μL of free formic acid and was removed newly the peptides by the used of the ZipTip$_{C18}$™. The peptides adherent to the ZipTip$_{C18}$™ were washed constantly with a de formic acid solution to 5% and subsequently avoid in a volume de 2-3 μL of a 60% acetonitrilo solución that contained a 1% formic acid The peptide created during the digestion were loaded in ones borosilicate capillars needles cover in gold introducing in the ionization fountain of the ortogonal geometric hibrido mass espectrometer equipment with a (QTOF-2™) nano-spray fountain.

ESI-MS mass spectrum were acquired in a range 350-2000 Da during 1 second. The signals most intense were selected to it's posterior ESI-MSMS sequence. The collision gas employee was the argon and it used a collisión energy appropriate to produce a extensive fragmentation of the peptides selected, that will allow it identification unequivocal in the data bases.

The ESI-MS espectum were deconvoluted and exported in a DTA format and import in the MASCOT programa to the identification of the protein in SWISSPROT and NCBInr data bases mediate the strategy of the Peptide Mass Fingerprint (PMF). To an exact identification of the protein it used a calibration inward to employee a peptide autoproteolitic of the trypsin and it fixed an error of 0.05 Da, to realice search of the peptides observed in the spectrum and it selected those signals that had an greater intensity to 10% of the intensity of the base peak.

Four peptides presents in the band analized were sequenced by ESI-MSMS (Tabla 4). These peptides PRZN_SERMA/PRZN_SERSP of the proteins concerning to the C-terminal region (indicate in red in the sequency of Table 6), previously identified in the anterior Examples.

TABLE 4

Peptides concerning to the p25 de *S. marcescens* that were sequenced by ESI-MSMS.

| # | Aminoacidic sequency | m/z teor. | m/z exp | Error |
|---|---|---|---|---|
| 1 | DFLSTTSNSQK (SEQ ID NO: 8) | 1226.51 | 1226.58 | 0.07 |
| 2 | SAASDSAPGASDWIR (SEQ ID NO: 9) | 1489.75 | 1489.68 | 0.07 |
| 3 | GGAGNDVLFGGGGADELWGGAGK (SEQ ID NO: 10) | 2060.96 | 2060.87 | 0.11 |
| 4 | TGDTVYGFNSNTGR (SEQ ID NO: 11) | 1488.65 | 1488.60 | 0.05 |

Likewise it founded others signals that although nor it sequenced, it's mass values concord very good with the expect of mass values to the tryptics peptides identified as PRZN_SERMA/PRZN_SERSP of the proteins C-terminal region, Table 5 (noted in blue in the Table 6). Between this peptides appear a loaded double signal that could to agree with the peptide of the PRZN_SERMA/PRZN_SERSP proteins C-terminal No it founded peptides that could be assignat to cuts specific of the PRZN_SERMA/PRZN_SERSP proteins N-terminal region

TABLE 5

Peptides tryptics belonging to the PRZN_SERMA protein detected in the ESI-MS espectrum.

| # | Aminoacidic Sequence | m/z exp. | m/z calc. | z | error |
|---|---|---|---|---|---|
| 1 | $^{325}$SFSDVGGLK$^{333}$ (SEQ ID NO: 12) | 455.20 | 455.24 | 2 | 0.04 |
| 2 | $^{417}$IDLSFFNK$^{424}$ (SEQ ID NO: 13) | 492.24 | 492.26 | 2 | 0.02 |
| 3 | $^{475}$IVGQVDVA TDFIV$^{487}$ (SEQ ID NO: 14) | 688.35 | 688.38 | 2 | 0.03 |

The methods and results exhibited in this example we able to secure that in the strongly anti-proliferative purified by DEAE chromatography of p25 band is present PRZN_SERMA/PRZN_SERSP. a C-terminal fragment of 25 kDa of the proteins

TABLE 6

Identification of the p50 and p25 obtained by DEAE chromatography.

```
PRZN_SERMA    MQSTKKAIEITESSLAAATTGYDAVDDLLHYHERGNGIQINGKDSFSNEQAGLFITRENQ
(SEQ ID NO: 15)
PRZN_SERSP    MQSTKKAIEITEGNPAAATTGYDAVDDLLHYHERGNGIQINGKDSFSNEQAGLFITRENQ
(SEQ ID NO: 16)
              ************  **********************************************

PRZN_SERMA    TWNGYKVFGQPVKLTFSFPDYKFSSTNVAGDTGLSKFSAEQQQQAKLSLQSWADVANITF
PRZN_SERSP    TWNGYKVFGQPVKLTFSFPDYKFSSTNVAGDTGLSKFSAEQQQQAKLSLQSWADVANITF
              ************************************************************

PRZN_SERMA    TEVAAGQKANITFGNYSQDRPGHYDYGTQAYAFLPNTIWQGQDLGGQTWYNVNQSNVKHP
PRZN_SERSP    TEVAAGQKANITFGNYSQDRPGHYDYGTQAYAFLPNTIWQGQDLGGQTWYNVNQSNVKHP
              ************************************************************

PRZN_SERMA    ATEDYGRQTFTHEIGHALGLSHPGDYNAGEGNPTYNDVTYAEDTRQFSLMSYWSETNTGG
PRZN_SERSP    ATEDYGRQTFTHEIGHALGLSHPGDYNAGEGNPTYRDVTYAEDTRQFSLMSYWSETNTGG
              **********************************  ************************

PRZN_SERMA    DNGGHYAAAPLLDDIAAIQHLYGANPSTRTGDTVYGFNSNTGRDFLSTTSNSQKVIFAAW
PRZN_SERSP    DNGGHYAAAPLLDDIAAIQHLYGANLSTRTGDTVYGFNSNTGRDFLSTTSNSQKVIFAAW
              ************************  **********************************

PRZN_SERMA    DAGGNDTFDFSGYTANQRINLNEKSFSDVGGLKGNVSIAAGVTIENAIGGSGNDVIVGNA
PRZN_SERSP    DAGGNDTFDFSGYTANQRINLNEKSFSDVGGLKGNVSIAAGVTIENAIG-FRQRLIVGNA
              *************************************************  *****

PRZN_SERMA    ANNVLKGGAGNDVLFGGGGADELWGGAGKDIFVFSAASDSAPGASDWIRDFQKGIDKIDL
PRZN_SERSP    ANNVLKGGAGNDVLFGGGGADELWGGAGKDIFVFSAASDSAPGASDWIRDFQKGIDKIDL
              ************************************************************

PRZN_SERMA    SFFNKEANSSDFIHFVDHFSGTAGEALLSYNASSNVTDLSVNIGGHQAPDFLVKIVGQVD
PRZN_SERSP    SFFNKEAQSSDFIHFVDHFSGAAGEALLSYNASNNVTDLSVNIGGHQAPDFLVKIVGQVD
              ***** ************** *********** ***************************

PRZN_SERMA    VATDFIV
PRZN_SERSP    VATDFIV
              *******
```

In the sequency are find fault with the aminoacids that aren't presents in the mature protein. without this aminoacids the molecular weight of PRZN_SERSP y PRZN_SERMA this proteins are respectively, 50595.4 Da 50293.4 Da.

The identification of the tryptics peptides that to defer between moleculas suggest that both species may be present and include coexistir (green (*italic*): identified by mass spectrometry and maroon (emphasize): identifed by Edman degradation inside of the continuous rectangle).

The peptides marking (┌┐ and ┌┐) were identified in the p25 obtained by the chromatography describe in the Example 6.

The peptides marking (┌┐) and underline were identified in the p50 obtained by the chromatography describe in Example 6 and the peptide in (*italic*) was identified from a gel fragment.

Example 15

Proteins of the N- y C-Terminal with 25 kDa

To determine the molecular size of the proteins that maybe co-existir to height of 25 kDa in SDS-PAGE, to part of degradation of PRZN_SERMA/PRZN_SER, are create it's sequence and were introduced in the GenRun program. The fragments correspond to N- y C-terminal of 25 kDa (±2 kDa) are showed in the Table 7.

TABLE 7

Proteins with size of 25 ± 2 kDa, fountain to partir of degradation of PRZN_SERMA/PRZN_SERSP. The molecular weigh was determined mediate the GenRun program, to part of the N-y C-terminal. Last.

| Protein | Sequence |
| --- | --- |
| ARA 1 (SEQ ID NO: 1) | MSYWSETNTGGDNGGHYAAAPLLDDIAAIQHLYGANPSTRTGDTVYGFNSNTGRDFLSTT SNSQKVIFAAWDAGGNDTFDFSGYTANQRINLNEKSFSDVGGLKGNVSIAAGVTIENAIG GSGNDVIVGNAANNVLKGGAGNDVLFGGGGADELWGGAGKDIFVFSAASDSAPGASDWIR DFQKGIDKIDLSFFNKEANSSDFIHFVDHFSGTAGEALLSYNASSNVTDLSVNIGGHQAP DFLVKIVGQVDVATDFIV |
| ARA2 (SEQ ID NO: 2) | MSYWSETNTGGDNGGHYAAAPLLDDIAAIQHLYGANLSTRTGDTVYGFNSNTGRDFLSTT SNSQKVIFAAWDAGGNDTFDFSGYTANQRINLNEKSFSDVGGLKGNVSIAAGVTIENAIG FRQRLIVGNAANNVLKGGAGNDVLFGGGGADELWGGAGKDIFVFSAASDSAPGASDWIRD FQKGIDKIDLSFFNKEAQSSDFIHFVDHFSGAAGEALLSYNASNNVTDLSVNIGGHQAPD FLVKIVGQVDVATDFIV |
| ARA3 (SEQ ID NO: 3) | TRTGDTVYGFNSNTGRDFLSTTSNSQKVIFAAWDAGGNDTFDFSGYTANQRINLNEKSFS DVGGLKGNVSIAAGVTIENAIGFRQRLIVGNAANNVLKGGAGNDVLFGGGGADELWGGAG KDIFVFSAASDSAPGASDWIRDFQKGIDKIDLSFFNKEAQSSDFIHFVDHFSGAAGEALL SYNASNNVTDLSVNIGGHQAPDFLVKIVGQVDVATDFIV |
| ARA4 (SEQ ID NO: 4) | TRTGDTVYGFNSNTGRDFLSTTSNSQKVIFAAWDAGGNDTFDFSGYTANQRINLNEKSFS DVGGLKGNVSIAAGVTIENAIGFRQRLIVGNAANNVLKGGAGNDVLFGGGGADELWGGAG KDIFVFSAASDSAPGASDWIRDFQKGIDKIDLSFFNKEAQSSDFIHFVDHFSGAAGEALL SYNASNNVTDLSVNIGGHQAPDFLVKIVGQVDVATDFIV |

Example 16

MG2327-Induced Apoptosis

MG2327 Induces Apoptosis on Mieloma X63 Cells, Involving Fragmented DNA and Including Mitochondria and Microtubules.

For determining the kind of tumoral cell death, murine mieloma P3X63Ag8 cells ($2*10^7$) were treated in vitro with MG2327 at 22 μg/mL. Treated and untreated cells were prepared for ultrastructural transmission electron microscopy studies at different times, and genomic DNA was extracted for DNA laddering assay.

DNA fragmentation was assessed by 2% agarose gel electrophoresis. Apoptosis frequently involves cellular DNA laddering of 180-200 bp, representative of inter-nucleosomal distances (Soldatenkov, V. A., Prasad, S., Voloshin, Y., and Dritschilo, A. 1998. Cell Death Differ. 5:307-12). As shown in FIG. 13, a significant increase was observed of oligonucleosomes, correlated to morphological changes in culture and corroborated by electron microscopy.

Inter-nucleosomal fragmentation was preceded by morphological signs of apoptosis detected by optical microscopy. Moreover, micrographs showed a altered citoplasmic organelles (mitochondrion, 2 h), also preceding chromatin condensation (4 h) and internucleosomal fragmentation (6 h).

MG2327 Affects Microtubules and the Ultrastructural Organization of Mitochondria, Increasing P3X63Ag8 Cells' Apoptosis.

Untreated cells showed a typical mitochondrial ultrastructure: clearly visible mitochondrial cristae and a mitochondrial matrix of higher density, evenly distributed all over the cytoplasm (FIG. 14A).

Cells treated with MG2327 showed increased size mitochondria, a lower matriz density and heavily affected cristae morphology (FIGS. 14B-E). These ultrastructural changes mostly indicate disfunctional organelles.

Moreover, we observed extensive cytoplasmic vacuoles, also regarding the endoplasmic reticulum as mitochondria and nuclear structure, 2 hrs after treatment (FIG. 14B).

Different morphological changes were observed in the nuclei at 6 hr treatment (chromatin condensing, merging and laddering). In the late phase apoptosis micrograph (8 hr) of P3X63Ag8 cells treated with MG2327, chromatin appeared compact (FIG. 14F). Budding was not detected at any time.

Interestingly, mitochondria on P3X63Ag8 cells treated for 2 hr were clustered at cytoplasmic membrane periphery (FIGS. 14B-E), resulting from microtubule disruption and interfered mitochondria transport along this organelle. (Schatten, H., and Lewis, M. L. 2001 Acta Astronaut. 49:399-418).

FIGS. 14C and D show greater mitochondria, also bearing condensed structures attached to the inner mitochondrial membranes. These structures would have been generated by successive cristae fusion. MG2327 could generate apoptosis by cytochrome c release into the cytosol after mitochondrial outer membrane swelling while increasing in size, followed by caspase activation and apoptosis (Green, D. R. and Reed, J. C. 1998. Science. Without increasing in size, cytochrome c could also be completely and quickly released from damaged cristae of the mitochondrion to the cytosol, through junctions between the intermembrane space and cristae after fusion (Scorrano, L., Ashiya, M., Buttle, K., Weiler, S., Oakes, S. A., Mannella, C. A. and Korsmeyer, S. J. 2002. Dev Cell. 2:55-67). The process described significantly amplified apoptosis signals generated by MG2327 into cells.

Example 17

P25 and P50 Induce Apoptosic

To discern the role of p25 and p50 in the apoptotic events induced by MG2327, they were individually administered to P3X63Ag8 cells at different concentrations and analized by electron microscopy. In all cases, chromatin condensing, damaged mitrocondria cristae and clustered mitocondria were detected. Indeed, apoptosis induction by MG2327 is linked to the effect of is these two proteins.

Example 18

Antiangiogenic Effect of MG2327 and the Anti-Proliferating Polypeptides

Development of Tubular Structures in Matrigel

Human micro-vasculature-derived human endotelial cells (HMEC) were assessed for endothelial cord formation on matrigel (Crum R, Szabo S, Folkman J. 1985. Science. 230: 1375-8; Vacca, A., Ribatti, D., Presta, M., Minischettti, M., lurlaro, M, Ria, R, Albini, A, Bussolino, F. and Dammaacco, F. 1999. Blood 93:3064) after culture under non-cytotoxic MG2327 and p25 and p50 concentrations (Sanz, L., Pascual, M., Muñoz, A., González, M. A., Salvador C H, Álvarez-Vallina L. 2002. Microvascular Research 63:335-339). Results considered the length of tubular structures and the number of interconnections between them, as calculated by using the Image-Pro Express 4.5 package. They indicated a significant inhibition (p<0.05, ANOVA) of differentiation or maturation of endotelial cells (FIG. 15) after treatment with the MG2327 preparation and its p25 and p50 fractions.

Example 19

Indirect Effect of MG2327 on Proliferating Cells

MG2327 Protects Balb/c Mice from Myeloid Tumor Implants.

For analyzing the protective activity of MG2327 against implanted tumors, Balb/c mice were inoculated (i.p.) with 1 mg/ml of this antitumoral preparation under different immunization schedules. Three doses were administered, one dose every week, and two doses every week during three weeks with at least three days between doses. A negative control group was inoculated with 1×PBS. Two millions of P3X63Ag8 myeloma cells were inoculated i.p. to the experimental groups (treated and control) 150 days after the first dose (5 months after). All mice from the negative control group died during the first 25 days, meanwhile 100% of the treated animals survived without tumors. (FIG. 16).

Example 20

The C-Terminal Domain of Other Serralisins has also Cytotoxic Effect, without Proteolytic Activity The ATCC14756 strain was cultivated under similar conditions as the CMIB4202 strain according to Example 2 and its culture supernatants were processed as described in Example 6. In both preparations we observed proteins at the levels of 50 kDa that eluted with 50 mM phosphate-0.2 M NaCl, pH 8.00. These proteins showed enzymatic activity that was inhibited with 10 mM of EDTA and recovered with 5 μM $Zn_2SO_4$. Both proteins were digested chemically with CNBr and the digestion pattern was similar, generating similar fragments of approximately 25 kDa, corresponding to the C-terminus of p50, from the internal methionine in the sequence to the end of the molecule.

The fragments obtained from the digestion were renatured with a change in buffer through dialysis for 48 hours. The biological activity of these fragments was tested in the cytotoxicity assay described here, using HEp.2 cells that were incubated for 72 hours in their presence. The fragments produced by the digestion, and lacking proteolytic activity, in the presence of 5 mM EDTA, presented a higher cytotoxic activity that was dose-dependent, approximately 2.5 times over that of the complete p50 molecule. These fragments, once their sequences are known, can also be obtained by chemical synthesis or by recombination techniques.

Example 21

Combination of Fragments of Serralisins with Antibodies or Antibody Fragments

The polypeptidic fragments obtained in Examples 6 and 20 were chemically conjugated with the monoclonal antibody CB/ior-CEA.1 (Tormo B et al. APMIS 97:1073-1080, 1989), with its variable regions, and with the antibody fragment obtained via recombinant DNA technology from its sequence (diabody) (patent WO 03/093315). The conjugated biomolecules were assayed on the human tumor cell lines LoVo (ATCC CCL-229), AsPC-1 (ATCC CRL-1682) and LS 174T (ATCC CL-188), all expressing CEA in culture, through an anti-proliferation assays similar to the one described in Example 3. The conjugated fragments were used at cytotoxic concentrations equivalent to those of un-conjugated fragments, with a dose-dependent response, while with the un-conjugated molecules no anti-proliferation response was observed. It was shown that the conjugated fragments were bound to CEA on the cells, using procedures as cell-ELISA, and indirect immunofluorescence (patent WO 03/093315). These results demonstrate that the conjugates described here can be used for the therapy and diagnosis of cancer.

Incorporation of Sequence Listing

Incorporated herein by reference in its entirety is the Sequence Listing for the application. The Sequence Listing is disclosed on a computer-readable ASCII text file and created on May 18, 2011. The sequence.txt file is 19.7 kb in size.

The invention claimed is:

1. A pharmaceutical composition comprising a fragment of a serralysin from *Serratia marcescens*, wherein the fragment consists of SEQ ID NO: 1, 2, 3 or 4, wherein said composition is capable of producing antitumoral effects.

2. The pharmaceutical composition according to claim 1, wherein said serralysin fragments are obtained from cell culture supernatants, by genetic manipulation or by chemical synthesis.

3. The pharmaceutical composition according to claim 1, comprising one of the fragments or a mixture of the fragments.

4. A fragment of a serralysin from *Serratia marcescens* wherein the fragment consists of SEQ ID NO: 1, 2, 3 or 4.

5. The serralysin fragment of claim 4, wherein said fragment has antitumoral activity.

6. The pharmaceutical composition according to claim 1, further comprising one or several prodigiosins, wherein said prodigiosins enhance the antitumoral activity of the mentioned composition.

* * * * *